United States Patent
Wu et al.

(10) Patent No.: US 7,867,744 B2
(45) Date of Patent: Jan. 11, 2011

(54) POLYPEPTIDES HAVING CELLOBIOHYDROLASE II ACTIVITY AND POLYNUCLEOTIDES ENCODING SAME

(75) Inventors: Wenping Wu, Beijing (CN); Lene Lange, Valby (DK); Dominique Aubert Skovlund, Copehnagen N (DK); Ye Liu, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 52 days.

(21) Appl. No.: 11/958,527

(22) Filed: Dec. 18, 2007

(65) Prior Publication Data

US 2008/0213835 A1 Sep. 4, 2008

Related U.S. Application Data

(62) Division of application No. 10/540,091, filed as application No. PCT/DK03/00914 on Dec. 19, 2003, now Pat. No. 7,348,168.

(60) Provisional application No. 60/435,100, filed on Dec. 20, 2002.

(51) Int. Cl.
C12N 9/24 (2006.01)
C12N 9/14 (2006.01)
C12N 9/42 (2006.01)
C12N 1/20 (2006.01)
C12N 15/70 (2006.01)
C12P 21/06 (2006.01)
C12P 7/10 (2006.01)
C07H 21/04 (2006.01)
C12D 3/00 (2006.01)

(52) U.S. Cl. .................. 435/200; 435/195; 435/209; 435/69.1; 435/165; 435/252.3; 435/320.1; 536/23.2; 510/320

(58) Field of Classification Search .................. None
See application file for complete search history.

(56) References Cited

U.S. PATENT DOCUMENTS 5,919,697 A * 7/1999 Salmon et al. ............ 435/263
6,114,158 A 9/2000 Li et al.

FOREIGN PATENT DOCUMENTS

| EP | 0 214 971 B1 | 4/1995 |
| EP | 851 031 | 7/1998 |
| EP | 0 953 644 | 11/1999 |
| WO | WO 85/04672 | 10/1985 |
| WO | WO 91/17244 | 11/1991 |
| WO | WO 99/01544 | 1/1999 |

OTHER PUBLICATIONS

Whisstock et al. Quaterly Reviews of Biophysics, 2003, "Prediction of protein function from protein sequence and structure", 36(3): 307-340.*
Teeri et al., Gene, vol. 51, pp. 43-52 (1987).
Hayashida et al., Appl Environ Microbiol., vol. 54, No. 6, pp. 1523-1529 (1988).
Database EMBL Accession No. AY075018 (2005).
Database GeneSeqP Access No. AAW44853 (1998).
Ankudimova et al, Biochemistry (Moscow) vol. 64, No. 9, pp. 1068-1073 (1999).
Eriksen et al, European Journal of Biochemistry, vol. 77, pp. 445-450 (1977).
Ganju et al, Biochimica et Biophysica Acta, vol. 993, pp. 266-274 (1989).
Maheshwari et al, Microbiology and Molecular Biology Reviews, vol. 64, No. 3, pp. 461-488 (2000).
Experimental Report by Terhi Puranen, pp. 1-3 (Mar. 18, 2010).

* cited by examiner

*Primary Examiner*—Robert B Mondesi
*Assistant Examiner*—Iqbal H Chowdhury
(74) *Attorney, Agent, or Firm*—Elias J. Lambiris

(57) ABSTRACT

The present invention relates to polypeptides having cellobiohydrolase II activity and polynucleotides having a nucleotide sequence which encodes for the polypeptides. The invention also relates to nucleic acid constructs, vectors, and host cells comprising the nucleic acid constructs as well as methods for producing and using the polypeptides.

4 Claims, No Drawings

POLYPEPTIDES HAVING CELLOBIOHYDROLASE II ACTIVITY AND POLYNUCLEOTIDES ENCODING SAME

CROSS-REFERENCE TO RELATED APPLICATIONS

This application is a divisional of U.S. application Ser. No. 10/540,091 filed Jun. 20, 2005, (now U.S. Pat. No. 7,348, 168), which is a 35 U.S.C. 371 national application of PCT/DK2003/000914 filed Dec. 19, 2003, which claims priority or the benefit under 35 U.S.C. 119 of U.S. provisional application No. 60/435,100 filed Dec. 20, 2002, the contents of which are fully incorporated herein by reference.

FIELD OF THE INVENTION

The present invention relates to polypeptides having cellobiohydrolase II (also referred to as CBH II or CBH 2) activity and polynucleotides having a nucleotide sequence which encodes for the polypeptides. The invention also relates to nucleic acid constructs, vectors, and host cells comprising the nucleic acid constructs as well as methods for producing and using the polypeptides.

BACKGROUND OF THE INVENTION

Cellulose is an important industrial raw material and a source of renewable energy. The physical structure and morphology of native cellulose are complex and the fine details of its structure have been difficult to determine experimentally. However, the chemical composition of cellulose is simple, consisting of D-glucose residues linked by beta-1,4-glycosidic bonds to form linear polymers with chains length of over 10,000 glycosidic residues.

In order to be efficient, the digestion of cellulose requires several types of enzymes acting cooperatively. At least three categories of enzymes are necessary to convert cellulose into glucose: endo (1,4)-beta-D-glucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose. Among these three categories of enzymes involved in the biodegradation of cellulose, cellobiohydrolases are the key enzymes for the degradation of native crystalline cellulose.

Exo-cellobiohydrolases (Cellobiohydrolase II or CBH II) refer to the cellobiohydrolases which degrade cellulose by hydrolyzing the cellobiose from the non-reducing end of the cellulose polymer chains. The cellobiohydrolase II group belongs to the same EC group, i.e., EC 3.2.1.91, as the cellobiohydrolase I group, the difference being that cellobiohydrolase I degrade cellulose by hydrolyzing the cellobiose from the reducing end of the cellulose polymer chains.

It is an object of the present invention to provide improved polypeptides having cellobiohydrolase II activity and polynucleotides encoding the polypeptides. The improved polypeptides may have improved specific activity and/or improved stability—in particular improved thermostability. The polypeptides may also have an improved ability to resist inhibition by cellobiose.

SUMMARY OF THE INVENTION

In a first aspect the present invention relates to a polypeptide having cellobiohydrolase 11 activity, selected from the group consisting of:

(a) a polypeptide comprising an amino acid sequence selected from the group consisting of:
  an amino acid sequence which has at least 75%, identity with the amino acid sequence shown as amino acids 1 to 477 of SEQ ID NO: 2,
  a polypeptide comprising an amino acid sequence selected from the group consisting of: an amino acid sequence which has at least 85% identity with the partial amino acid sequence shown as amino acids 1 to 82 of SEQ ID NO: 4,
  a polypeptide comprising an amino acid sequence selected from the group consisting of: an amino acid sequence which has at least 85% identity with the partial amino acid sequence shown as amino acids 1 to 420 of SEQ ID NO: 4,
  a polypeptide comprising an amino acid sequence selected from the group consisting of: an amino acid sequence which has at least 80% identity with the partial amino acid sequence shown as amino acids 1 to 139 of SEQ ID NO: 6,
  a polypeptide comprising an amino acid sequence selected from the group consisting of: an amino acid sequence which has at least 95% identity with the partial amino acid sequence shown as amino acids 1 to 102 of SEQ ID NO: 8,
  a polypeptide comprising an amino acid sequence selected from the group consisting of: an amino acid sequence which has at least 85% identity with the partial amino acid sequence shown as amino acids 1 to 144 of SEQ ID NO: 10,
  a polypeptide comprising an amino acid sequence selected from the group consisting of: an amino acid sequence which has at least 75% identity with the partial amino acid sequence shown as amino acids 1 to 99 of SEQ ID NO: 12,
  a polypeptide comprising an amino acid sequence selected from the group consisting of: an amino acid sequence which has at least 85% identity with the partial amino acid sequence shown as amino acids 1 to 140 of SEQ ID NO: 14,
  a polypeptide comprising an amino acid sequence selected from the group consisting of: an amino acid sequence which has at least 75% identity with the partial amino acid sequence shown as amino acids 1 to 109 of SEQ ID NO: 16,
  a polypeptide comprising an amino acid sequence selected from the group consisting of: an amino acid sequence which has at least 75% identity with the amino acid sequence shown as SEQ ID NO: 16,
  a polypeptide comprising an amino acid sequence selected from the group consisting of: an amino acid sequence which has at least 75% identity with the partial amino acid sequence shown as amino acids 1 to 143 of SEQ ID NO: 18,
  a polypeptide comprising an amino acid sequence selected from the group consisting of: an amino acid sequence which has at least 70% identity with the partial amino acid sequence shown as amino acids 1 to 71 of SEQ ID NO: 20,
  a polypeptide comprising an amino acid sequence selected from the group consisting of: an amino acid sequence which has at least 60% identity with the amino acid sequence shown as amino acids 1 to 220 of SEQ ID NO: 22,
  a polypeptide comprising an amino acid sequence selected from the group consisting of: an amino acid sequence which has at least 65% identity with the amino acid sequence shown as amino acids 1 to 458 of SEQ ID NO: 24, and a polypeptide comprising an amino acid sequence selected from the group consisting of: an amino acid sequence which has at least 70% identity with the amino acid sequence shown as amino acids 1 to 390 of SEQ ID NO: 26;

(b) a polypeptide comprising an amino acid sequence selected from the group consisting of:

an amino acid sequence which has at least 75% identity with the polypeptide encoded by the cellobiohydrolase II encoding part of the nucleotide sequence present in *Chaetomium thermophilum*, a polypeptide comprising an amino acid sequence selected from the group consisting of: an amino acid sequence which has at least 85% identity with the polypeptide encoded by the cellobiohydrolase II encoding part of the nucleotide sequence present in *Myceliophtora thermophila*, a polypeptide comprising an amino acid sequence selected from the group consisting of: an amino acid sequence which has at least 80% identity with the polypeptide encoded by an amino acid sequence which has at least 80% identity with the polypeptide encoded by the cellobiohydrolase II encoding part of the nucleotide sequence present in *Acremonium thermophilum*, an amino acid sequence which has at least 95% identity with the polypeptide encoded by the cellobiohydrolase II encoding part of the nucleotide sequence present in *Melanocarpus* sp., an amino acid sequence which has at least 85% identity with the polypeptide encoded by the cellobiohydrolase II encoding part of the nucleotide sequence present in *Thielavia microspora*, an amino acid sequence which has at least 75% identity with the polypeptide encoded by the cellobiohydrolase II encoding part of the nucleotide sequence present in *Aspergillus* sp., an amino acid sequence which has at least 85% identity with the polypeptide encoded by the cellobiohydrolase II encoding part of the nucleotide sequence present in *Thielavia australiensis*, an amino acid sequence which has at least 75% identity with the polypeptide encoded by the cellobiohydrolase II encoding part of the nucleotide sequence present in *Aspergillus tubingensis*, an amino acid sequence which has at least 75% identity with the polypeptide encoded by the cellobiohydrolase II encoding part of the nucleotide sequence present in *Gloeophyllum trabeum*, an amino acid sequence which has at least 70% identity with the polypeptide encoded by the cellobiohydrolase II encoding part of the nucleotide sequence present in *Meripilus giganteus*, an amino acid sequence which has at least 60% identity with the polypeptide encoded by the cellobiohydrolase II encoding part of the nucleotide sequence present in *Trichophaea saccata*, an amino acid sequence which has at least 65% identity with the polypeptide encoded by the cellobiohydrolase II encoding part of the nucleotide sequence present in *Stilbella annulata*, and an amino acid sequence which has at least 70% identity with the polypeptide encoded by the cellobiohydrolase II encoding part of the nucleotide sequence present in *Malbrancheae cinnamomeal*;

(c) a polypeptide comprising an amino acid sequence selected from the group consisting of:

an amino acid sequence which has at least 75% identity with the polypeptide encoded by nucleotides 63 to 1493 of SEQ ID NO: 1, a polypeptide comprising an amino acid sequence selected from the group consisting of: an amino acid sequence which has at least 85% identity with the polypeptide encoded by nucleotides 1 to 246 of SEQ ID NO: 3, a polypeptide comprising an amino acid sequence selected from the group consisting of: an amino acid sequence which has at least 85% identity with the polypeptide encoded by nucleotides 1 to 1272 of SEQ ID NO: 3, a polypeptide comprising an amino acid sequence selected from the group consisting of: an amino acid sequence which has at least 80% identity with the polypeptide encoded by nucleotides 1 to 417 of SEQ ID NO: 5, a polypeptide comprising an amino acid sequence selected from the group consisting of: an amino acid sequence which has at least 95% identity with the polypeptide encoded by nucleotides 1 to 306 of SEQ ID NO: 7, a polypeptide comprising an amino acid sequence selected from the group consisting of: an amino acid sequence which has at least 85% identity with the polypeptide encoded by nucleotides 1 to 432 of SEQ ID NO: 9, a polypeptide comprising an amino acid sequence selected from the group consisting of: an amino acid sequence which has at least 75% identity with the polypeptide encoded by nucleotides 1 to 297 of SEQ ID NO: 11, a polypeptide comprising an amino acid sequence selected from the group consisting of: an amino acid sequence which has at least 85% identity with the polypeptide encoded by nucleotides 1 to 420 of SEQ ID NO: 13, a polypeptide comprising an amino acid sequence selected from the group consisting of: an amino acid sequence which has at least 75% identity with the polypeptide encoded by nucleotides 1 to 330 of SEQ ID NO: 15, a polypeptide comprising an amino acid sequence selected from the group consisting of: an amino acid sequence which has at least 75% identity with the polypeptide encoded by nucleotides 1 to 1221 of SEQ ID NO: 15, a polypeptide comprising an amino acid sequence selected from the group consisting of: an amino acid sequence which has at least 75% identity with the polypeptide encoded by nucleotides 1 to 1221 of SEQ ID NO: 15, a polypeptide comprising an amino acid sequence selected from the group consisting of: an amino acid sequence which has at least 75% identity with the polypeptide encoded by nucleotides 1 to 429 of SEQ ID NO: 17, a polypeptide comprising an amino acid sequence selected from the group consisting of: an amino acid sequence which has at least 70% identity with the polypeptide encoded by nucleotides 1 to 213 of SEQ ID NO: 19, a polypeptide comprising an amino acid sequence selected from the group consisting of: an amino acid sequence which has at least 60% identity with the polypeptide encoded by nucleotides 43 to 701 of SEQ ID NO: 21, a polypeptide comprising an amino acid sequence selected from the group consisting of: an amino acid sequence which has at least 65% identity with the polypeptide encoded by nucleotides 21 to 1394 of SEQ ID NO: 23, and a polypeptide comprising an amino acid sequence selected from the group consisting of: an amino acid sequence which has at least 70% identity with the polypeptide encoded by nucleotides 41 to 1210 of SEQ ID NO: 25;

(d) a polypeptide which is encoded by a nucleotide sequence which hybridizes under high stringency conditions with a polynucleotide probe selected from the group consisting of
(i) the complementary strand of the nucleotides selected from the group consisting of
nucleotides 63 to 1493 of SEQ ID NO: 1,
nucleotides 1 to 246 of SEQ ID NO: 3,
nucleotides 1 to 1272 of SEQ ID NO: 3,
nucleotides 1 to 417 of SEQ ID NO: 5,
nucleotides 1 to 306 of SEQ ID NO: 7,
nucleotides 1 to 432 of SEQ ID NO: 9,
nucleotides 1 to 297 of SEQ ID NO: 11,
nucleotides 1 to 420 of SEQ ID NO: 13,
nucleotides 1 to 330 of SEQ ID NO: 15,
nucleotides 1 to 1221 of SEQ ID NO: 15,
nucleotides 1 to 429 of SEQ ID NO: 17,
nucleotides 1 to 213 of SEQ ID NO: 19,
nucleotides 43 to 701 of SEQ ID NO: 21,
nucleotides 21 to 1394 of SEQ ID NO: 23, and
nucleotides 41 to 1210 of SEQ ID NO: 25;
(ii) the complementary strand of the nucleotides selected from the group consisting of
nucleotides 63 to 563 of SEQ ID NO: 1,
nucleotides 43 to 543 of SEQ ID NO: 21,
nucleotides 21 to 521 of SEQ ID NO: 23, and
nucleotides 41 to 541 of SEQ ID NO: 25;
(iii) the complementary strand of the nucleotides selected from the group consisting of:
nucleotides 63 to 263 of SEQ ID NO: 1,
nucleotides 1 to 200 of SEQ ID NO: 3,
nucleotides 1 to 200 of SEQ ID NO: 5,
nucleotides 1 to 200 of SEQ ID NO: 7,
nucleotides 1 to 200 of SEQ ID NO: 9,
nucleotides 1 to 200 of SEQ ID NO: 11,
nucleotides 1 to 200 of SEQ ID NO: 13,
nucleotides 1 to 200 of SEQ ID NO: 15,
nucleotides 1 to 1221 of SEQ ID NO: 15,
nucleotides 1 to 200 of SEQ ID NO: 17,
nucleotides 1 to 200 of SEQ ID NO: 19,
nucleotides 43 to 243 of SEQ ID NO: 21,
nucleotides 21 to 221 of SEQ ID NO: 23, and
nucleotides 41 to 241 of SEQ ID NO: 25; and
(e) a fragment of (a), (b) or (c) that has cellobiohydrolase II activity.

In a second aspect the present invention relates to a polynucleotide having a nucleotide sequence which encodes for the polypeptide of the invention.

In a third aspect the present invention relates to a nucleic acid construct comprising the nucleotide sequence, which encodes for the polypeptide of the invention, operably linked to one or more control sequences that direct the production of the polypeptide in a suitable host.

In a fourth aspect the present invention relates to a recombinant expression vector comprising the nucleic acid construct of the invention.

In a fifth aspect the present invention relates to a recombinant host cell comprising the nucleic acid construct of the invention.

In a sixth aspect the present invention relates to a method for producing a polypeptide of the invention, the method comprising:
(a) cultivating a strain, which in its wild-type form is capable of producing the polypeptide, to produce the polypeptide; and (b) recovering the polypeptide.

In a seventh aspect the present invention relates to a method for producing a polypeptide of the invention, the method comprising:
(a) cultivating a recombinant host cell of the invention under conditions conducive for production of the polypeptide; and
(b) recovering the polypeptide.

In an eight aspect the present invention relates to a method for in-situ production of a polypeptide of the invention, the method comprising:
(a) cultivating a recombinant host cell of the invention under conditions conducive for production of the polypeptide; and
(b) contacting the polypeptide with a desired substrate without prior recovery of the polypeptide.

Other aspects of the present invention will be apparent from the below description and from the appended claims.

DEFINITIONS

Prior to discussing the present invention in further details, the following terms and conventions will first be defined:

Substantially pure polypeptide: In the present context, the term "substantially pure polypeptide" means a polypeptide preparation which contains at the most 10% by weight of other polypeptide material with which it is natively associated (lower percentages of other polypeptide material are preferred, e.g., at the most 8% by weight, at the most 6% by weight, at the most 5% by weight, at the most 4% at the most 3% by weight, at the most 2% by weight, at the most 1% by weight, and at the most 0.5% by weight). Thus, it is preferred that the substantially pure polypeptide is at least 92% pure, i.e., that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e., that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

Cellobiohydrolase II activity: The term "cellobiohydrolase II activity" is defined herein as a cellulose 1,4-beta-cellobiosidase (also referred to as Exo-glucanase, Exo-cellobiohydrolase or 1,4-beta-cellobiohydrolase) activity, as defined in the enzyme class EC 3.2.1.91 or CAZy Family Glycoside Hydrolase Family 6, which catalyzes the hydrolysis of 1,4-beta-D-glucosidic linkages in cellulose and cellotetraose, releasing cellobiose from the non-reducing ends of the chains.

For purposes of the present invention, cellobiohydrolase II activity may be determined according to the procedure described in Example 6.

In an embodiment, cellobiohydrolase II activity may be determined according to the procedure described in Deshpande M V et al., *Methods in Enzymology*, pp. 126-130 (1988): "Selective Assay for Exo-1,4-Beta-Glucanases". According to this procedure, one unit of cellobiohydrolase II activity (agluconic bond cleavage activity) is defined as 1.0 micromole of p-nitrophenol produced per minute at 50° C., pH 5.0. The polypeptides of the present invention should preferably have at least 20% of the cellobiohydrolase II activity of a polypeptide consisting of an amino acid sequence selected from the group consisting of SEQ ID NO: 2, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26. In a particular preferred embodiment the polypeptides should have at least 40%, such as at least 50%, preferably at least 60%, such as at least 70%, more preferably at least 80%, such as at least 90%, most preferably at least 95%, such as about or at least 100% of the cellobiohydrolase II activity of the polypeptide consisting of the amino acid sequence selected from the group consisting of:

amino acids 1 to 477 of SEQ ID NO: 2,
amino acids 1 to 82 of SEQ ID NO: 4,
amino acids 1 to 420 of SEQ ID NO: 4,
amino acids 1 to 139 of SEQ ID NO: 6,
amino acids 1 to 102 of SEQ ID NO: 8,
amino acids 1 to 144 of SEQ ID NO: 10,
amino acids 1 to 99 of SEQ ID NO: 12,
amino acids 1 to 140 of SEQ ID NO: 14,
amino acids 1 to 109 of SEQ ID NO: 16,
amino acids 1 to 407 of SEQ ID NO: 16,
amino acids 1 to 143 of SEQ ID NO: 18,
amino acids 1 to 71 of SEQ ID NO: 20,
amino acids 1 to 220 of SEQ ID NO: 22,
amino acids 1 to 458 of SEQ ID NO: 24, and
amino acids 1 to 390 of SEQ ID NO: 26.

Identity: In the present context, the homology between two amino acid sequences or between two nucleotide sequences is described by the parameter "identity".

For purposes of the present invention, the degree of identity between two amino acid sequences is determined by using the program FASTA included in version 2.0x of the FASTA program package (see Pearson and Lipman, 1988, "Improved Tools for Biological Sequence Analysis", *PNAS* 85:2444-2448; and Pearson, 1990, "Rapid and Sensitive Sequence Comparison with FASTP and FASTA", *Methods in Enzymology* 183:63-98). The scoring matrix used was BLOSUM50, gap penalty was −12, and gap extension penalty was −2.

The degree of identity between two nucleotide sequences is determined using the same algorithm and software package as described above. The scoring matrix used was the identity matrix, gap penalty was −16, and gap extension penalty was −4.

Fragment: When used herein, a "fragment" of a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26 is a polypeptide having one or more amino acids deleted from the amino and/or carboxyl terminus of this amino acid sequence.

Allelic variant: In the present context, the term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially sure polynucleotide: The term "substantially pure polynucleotide" as used herein refers to a polynucleotide preparation, wherein the polynucleotide has been removed from its natural genetic milieu, and is thus free of other extraneous or unwanted coding sequences and is in a form suitable for use within genetically engineered protein production systems. Thus, a substantially pure polynucleotide contains at the most 10% by weight of other polynucleotide material with which it is natively associated (lower percentages of other polynucleotide material are preferred, e.g., at the most 8% by weight, at the most 6% by weight, at the most 5% by weight, at the most 4% at the most 3% by weight, at the most 2% by weight, at the most 1% by weight, and at the most 0.5% by weight). A substantially pure polynucleotide may, however, include naturally occurring 5' and 3' untranslated regions, such as promoters and terminators. It is preferred that the substantially pure polynucleotide is at least 92% pure, i.e., that the polynucleotide constitutes at least 92% by weight of the total polynucleotide material present in the preparation, and higher percentages are preferred such as at least 94% pure, at least 95% pure, at least 96% pure, at least 96% pure, at least 97% pure, at least 98% pure, at least 99%, and at the most 99.5% pure. The polynucleotides disclosed herein are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form".

Modification(s): In the context of the present invention the term "modification(s)" is intended to mean any chemical modification of a polypeptide consisting of an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26, as well as genetic manipulation of the DNA encoding that polypeptide. The modification(s) can be replacement(s) of the amino acid side chain(s), substitution(s), deletion(s) and/or insertions(s) in or at the amino acid(s) of interest.

Artificial variant: When used herein, the term "artificial variant" means a polypeptide having cellobiohydrolase II activity, which has been produced by an organism which is expressing a modified gene as compared to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, and SEQ ID NO: 25. The modified gene, from which said variant is produced when expressed in a suitable host, is obtained through human intervention by modification of a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, and SEQ ID NO: 25.

cDNA: The term "cDNA" when used in the present context, is intended to cover a DNA molecule which can be prepared by reverse transcription from a mature, spliced, mRNA molecule derived from a eukaryotic cell. cDNA lacks the intron sequences that are usually present in the corresponding genomic DNA. The initial, primary RNA transcript is a precursor to mRNA and it goes through a series of processing events before appearing as mature spliced mRNA. These events include the removal of intron sequences by a process called splicing. When cDNA is derived from mRNA it therefore lacks intron sequences.

Nucleic acid construct: When used herein, the term "nucleic acid construct" means a nucleic acid molecule, either single- or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" is defined herein as a configuration in which a control sequence is appropriately placed at a position relative to the coding sequence of the DNA sequence such that the control sequence directs the expression of a polypeptide.

Coding sequence: When used herein the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes DNA, cDNA, and recombinant nucleotide sequences.

Expression: In the present context, the term "expression" includes any step involved in the production of the polypeptide including, but not limited to, transcription, post-transcriptional modification, translation, post-translational modification, and secretion.

Expression vector: In the present context, the term "expression vector" covers a DNA molecule, linear or circular, that comprises a segment encoding a polypeptide of the invention, and which is operably linked to additional segments that provide for its transcription.

Host cell: The term "host cell", as used herein, includes any cell type which is susceptible to transformation with a nucleic acid construct.

The terms "polynucleotide probe", "hybridization" as well as the various stringency conditions are defined in the section entitled "Polypeptides Having Cellobiohydrolase II Activity".

Thermostability: The term "thermostability", as used herein, is measured as described in Example 2.

DETAILED DESCRIPTION OF THE INVENTION

Polypeptides Having Cellobiohydrolase II Activity

In a first embodiment, the present invention relates to polypeptides having cellobiohydrolase II activity and where the polypeptides comprises, preferably consists of, an amino acid sequence which has a degree of identity to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26., (i.e., the mature polypeptide) of at least 65%, preferably at least 70%, e.g., at least 75%, more preferably at least 80%, such as at least 85%, even more preferably at least 90%, most preferably at least 95%, e.g., at least 96%, such as at least 97%, and even most preferably at least 98%, such as at least 99% (hereinafter "homologous polypeptides"). In an interesting embodiment, the amino acid sequence differs by at the most ten amino acids (e.g., by ten amino acids), in particular by at the most five amino acids (e.g., by five amino acids), such as by at the most four amino acids (e.g., by four amino acids), e.g., by at the most three amino acids (e.g., by three amino acids) from an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26. In a particular interesting embodiment, the amino acid sequence differs by at the most two amino acids (e.g., by two amino acids), such as by one amino acid from an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26.

Preferably, the polypeptides of the present invention comprise an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26; an allelic variant thereof; or a fragment thereof that has cellobiohydrolase II activity. In another preferred embodiment, the polypeptide of the present invention consists of an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26.

The polypeptide of the invention may be a wild-type cellobiohydrolase II identified and isolated from a natural source. Such wild-type polypeptides may be specifically screened for by standard techniques known in the art, such as molecular screening as described in Example 1. Furthermore, the polypeptide of the invention may be prepared by the DNA shuffling technique, such as described in Ness et al., 1999, *Nature Biotechnology* 17: 893-896. Moreover, the polypeptide of the invention may be an artificial variant which comprises, preferably consists of, an amino acid sequence that has at least one substitution, deletion and/or insertion of an amino acid as compared to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26. Such artificial variants may be constructed by standard techniques known in the art, such as by site-directed/random mutagenesis of the polypeptide comprising an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26. In one embodiment of the invention, amino acid changes (in the artificial variant as well as in wild-type polypeptides) are of a minor nature, that is conservative amino acid substitutions that do not significantly affect the folding and/or activity of the protein; small deletions, typically of one to about 30 amino acids; small amino or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by Neurath and Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In an interesting embodiment of the invention, the amino acid changes are of such a nature that the physico-chemical properties of the polypeptides are altered. For example, amino acid changes may be performed, which improve the thermal stability of the polypeptide, which alter the substrate specificity, which changes the pH optimum, and the like.

Preferably, the number of such substitutions, deletions and/or insertions as compared to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26 is at the most 10, such as at the most 9, e.g., at the most 8, more preferably at the most 7, e.g., at the most 6, such as at the most 5, most preferably at the most 4, e.g., at the most 3, such as at the most 2, in particular at the most 1.

The present inventors have isolated nucleotide sequences encoding polypeptides having cellobiohydrolase II activity from the microorganisms selected from the group consisting of *Chaetomium thermophilum, Myceliophthora thermophila, Acremonium thermophilum, Thielavia australiensis, Thielavia microspore, Aspergillus tubingensis, Aspergillus tubingensis* syn. *Aspergillus neotubingensis Frisvad* sp. nov., *Gloeophyllum trabeum, Meripilus giganteus, Trichophaea saccata, Stilbella annulata, Stilbella annulata* and *Malbrancheae cinnamomea*.

Thus, in a second embodiment, the present invention relates to polypeptides comprising an amino acid sequence which has at least 65% identity with the polypeptide encoded by the cellobiohydrolase II encoding part of the nucleotide sequence present in an organism selected from the group consisting of *Chaetomium thermophilum* CGMCC 0859, *Myceliophthora thermophila* CGMCC 0862, *Myceliophthora thermophila* CGMCC 0862, *Acremonium* sp. T178-4 CGMCC 0857, *Acremonium* sp. T178-4, *Melanocarpus* sp. CGMCC 0861, *Thielavia microspora* CGMCC 0863, *Aspergillus* sp. T186-2 CGMCC 0858, *Thielavia australiensis* CGMCC 0864, *Gloeophyllum trabeum* ATCC 11.39, *Aspergillus tubingensis*, CBS 161.79, *Trichophaea saccata*, CBS 804.70, *Stilbella annulata* CBS 185.70, and *Malbranchea cinnamomea*, CBS 115.68. In an interesting embodiment of the invention, the polypeptide comprises an amino acid sequence which has at least 70%, e.g., at least 75%, preferably at least 80%, such as at least 85%, more preferably at least 90%, most preferably at least 95%, e.g., at least 96%, such as at least 97%, and even most preferably at least 98%, such as at least 99% identity with the polypeptide encoded by the cellobiohydrolase II encoding part of the nucleotide sequence present in an organism selected from the group consisting of *Chaetomium thermophilum* CGMCC 0859, *Myceliophthora thermophila* CGMCC 0862, *Myceliophthora thermophila* CGMCC 0862, *Acremonium* sp. T178-4 CGMCC 0857, *Acremonium* sp. T178-4, *Melanocarpus* sp. CGMCC 0861, *Thielavia microspora* CGMCC 0863, *Aspergillus* sp. T186-2 CGMCC 0858, *Thielavia australiensis* CGMCC 0864, *Gloeophyllum trabeum* ATCC 11.39, *Aspergillus tubingensis*, CBS 161.79, *Trichophaea saccata*, CBS 804.70, *Stilbella annulata* CBS 185.70, and *Malbranchea cinnamomea*, CBS 115.68 (hereinafter "homologous polypeptides"). In an interesting embodiment, the amino acid sequence differs by at the most ten amino acids (e.g., by ten amino acids), in particular by at the most five amino acids (e.g., by five amino acids), such as by at the most four amino acids (e.g., by four amino acids), e.g., by at the most three amino acids (e.g., by three amino acids) from the polypeptide encoded by the cellobiohydrolase II encoding part of the nucleotide sequence present in an organism selected from the group consisting of *Chaetomium thermophilum* CGMCC 0859, *Myceliophthora thermophila* CGMCC 0862, *Myceliophthora thermophila* CGMCC 0862, *Acremonium* sp. T178-4 CGMCC 0857, *Acremonium* sp. T178-4, *Melanocarpus* sp. CGMCC 0861, *Thielavia microspora* CGMCC 0863, *Aspergillus* sp. T1862 CGMCC 0858, *Thielavia australiensis* CGMCC 0864, Gloeophyllum trabeum ATCC 11.39, *Aspergillus tubingensis* CBS 161.79, *Trichophaea saccata* CBS 804.70, *Stilbella annulata* CBS 185.70, and *Malbranchea cinnamomea* CBS 115.68. In a particular interesting embodiment, the amino acid sequence differs by at the most two amino acids (e.g., by two amino acids), such as by one amino acid from the polypeptide encoded by the cellobiohydrolase II encoding part of the nucleotide sequence present in an organism selected from the group consisting of *Chaetomium thermophilum* CGMCC 0859, *Myceliophthora thermophila* CGMCC 0862, *Myceliophthora thermophila* CGMCC 0862, *Acremonium* sp. T178-4 CGMCC 0857, *Acremonium* sp. T178-4, *Melanocarpus* sp. CGMCC 0861, *Thielavia microspora* CGMCC 0863, *Aspergillus* sp. T186-2 CGMCC 0858, *Thielavia australiensis* CGMCC 0864, *Gloeophyllum trabeum* ATCC 11.39, *Aspergillus tubingensis* CBS 161.79, *Trichophaea saccata* CBS 804.70, *Stilbella annulata* CBS 185.70, and *Malbranchea cinnamomea* CBS 115.68.

In a third embodiment, the present invention relates to polypeptides having cellobiohydrolase II activity which are encoded by nucleotide sequences which hybridize under very low stringency conditions, preferably under low stringency conditions, more preferably under medium stringency conditions, more preferably under medium-high stringency conditions, even more preferably under high stringency conditions, and most preferably under very high stringency conditions with a polynucleotide probe selected from the group consisting of the complementary strand of the nucleotides selected from the group consisting of:

nucleotides 63 to 1493 of SEQ ID NO: 1,
nucleotides 1 to 246 of SEQ ID NO: 3,
nucleotides 1 to 417 of SEQ ID NO: 5,
nucleotides 1 to 306 of SEQ ID NO: 7,
nucleotides 1 to 432 of SEQ ID NO: 9,
nucleotides 1 to 297 of SEQ ID NO: 11,
nucleotides 1 to 420 of SEQ ID NO: 13,
nucleotides 1 to 330 of SEQ ID NO: 15,
nucleotides 1 to 1221 of SEQ ID NO: 15,
nucleotides 1 to 429 of SEQ ID NO: 17,
nucleotides 1 to 213 of SEQ ID NO: 19, nucleotides 43 to 701 of SEQ ID NO: 21,
nucleotides 21 to 1394 of SEQ ID NO: 23, and
nucleotides 41 to 1210 of SEQ ID NO: 25.

In another embodiment, the present invention relates to polypeptides having cellobiohydrolase II activity which are encoded by the cellobiohydrolase II encoding part of the nucleotide sequence present in a microorganism selected from the group consisting of:

a microorganism belonging to the family Chaetomiaceae, preferably to the genus *Chaetomium*, more preferably to the species *Chaetomium thermophilum*, a microorganism belonging to the genus *Myceliophthora*, preferably to the species *Myceliophthora thermophila*, a microorganism belonging to the species *Acremonium thermophilum*, a microorganism belonging to the family Chaetomiaceae, preferably to the genus *Thielavia*, preferably to the species *Thielavia australiensis*, a microorganism belonging to the genus *Aspergillus*, preferably belonging to the black *Aspergilli*, a microorganism belonging to the family Chaetomiaceae, preferably to the genus *Thielavia*, preferably to the species *Thielavia microspore*, a microorganism belonging to the genus *Aspergillus*, preferably belonging to the black *Aspergilli*, more preferably to the species *Aspergillus tubingensis*, and most preferably to the species *A. neotubingensis* Frisvad sp. nov.

a microorganism belonging to the Polyporales, preferably belonging to the family Fomitopsidacea, more preferably belonging to the genus *Gloeophyllum*, most preferably to the species *Gloeophyllum trabeum*, a microorganism belonging to the Hymenochaetales, preferably belonging to the family Rigidiporaceae, preferably belonging to the genus *Meripilus*, more preferably to the species *Meripilus giganteus*, a microorganism belonging to the Pezizomycotina, preferably belonging to Pezizales, preferably belonging to the family Pyronemataceae or the family Sarcosomataceae, more preferably belonging to the genus *Trichophaea* or the genus *Pseudoplectania*, most preferably *Trichophaea saccata*, a microorganism belonging to the species *Stilbella annulata*, and a microorganism belonging to the species *Malbrancheae cinnamomea*.

A nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, and SEQ ID NO: 23, and SEQ ID NO: 25 or a subsequence thereof, as well as an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26, or a fragment thereof, may be used to design a polynucleotide probe to identify and clone DNA encoding polypeptides having cellobiohydrolase 11 activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, more preferably at least 35 nucleotides in length, such as at least 70 nucleotides in length. It is, however, preferred that the polynucleotide probe is at least 100 nucleotides in length. For example, the polynucleotide probe may be at least 200 nucleotides in length, at least 300 nucleotides in length, at least 400 nucleotides in length or at least 500 nucleotides in length. Even longer probes may be used, e.g., polynucleotide probes which are at least 600 nucleotides in length, at least 700 nucleotides in length, at least 800 nucleotides in length, or at least 900 nucleotides in length. Both DNA and RNA probes can be used. The probes are typically labeled for detecting the corresponding gene (for example, with $^{32}$P, $^{3}$H, $^{35}$S, biotin, or avidin).

Thus, a genomic DNA or cDNA library prepared from such other organisms may be screened for DNA which hybridizes with the probes described above and which encodes a polypeptide having cellobiohydrolase II activity. Genomic or other DNA from such other organisms may be separated by agarose or polyacrylamide gel electrophoresis, or other separation techniques. DNA from the libraries or the separated DNA may be transferred to, and immobilized, on nitrocellulose or other suitable carrier materials. In order to identify a clone or DNA which is homologous with one of the sequence shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, and SEQ ID NO: 25, the carrier material with the immobilized DNA is used in a Southern blot.

For purposes of the present invention, hybridization indicates that the nucleotide sequence hybridizes to a labeled polynucleotide probe which hybridizes to any of the nucleotide sequences shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, and SEQ ID NO: 25 under very low to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

In an interesting embodiment, the polynucleotide probe is the complementary strand of the nucleotides selected from the group consisting of:
nucleotides 63 to 1493 of SEQ ID NO: 1,
nucleotides 1 to 246 of SEQ ID NO: 3,
nucleotides 1 to 1272 of SEQ ID NO: 3,
nucleotides 1 to 417 of SEQ ID NO: 5,
nucleotides 1 to 306 of SEQ ID NO: 7,
nucleotides 1 to 432 of SEQ ID NO: 9,
nucleotides 1 to 297 of SEQ ID NO: 11,
nucleotides 1 to 420 of SEQ ID NO: 13,
nucleotides 1 to 330 of SEQ ID NO: 15,
nucleotides 1 to 1221 of SEQ ID NO: 15,
nucleotides 1 to 429 of SEQ ID NO: 17,
nucleotides 1 to 213 of SEQ ID NO: 19,
nucleotides 43 to 701 of SEQ ID NO: 21,
nucleotides 21 to 1394 of SEQ ID NO: 23, and
nucleotides 41 to 1210 of SEQ ID NO: 25.

In another interesting embodiment, the polynucleotide probe is the complementary strand of the nucleotide sequence which encodes a polypeptide selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26. In a further interesting embodiment, the polynucleotide probe is the complementary strand of a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

For long probes of at least 100 nucleotides in length, very low to very high stringency conditions are defined as prehybridization and hybridization at 42° C. in 5×SSPE, 1.0% SDS, 5×Denhardt's solution, 100 microg/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 2×SSC, 0.1% SDS at 42° C. (very low stringency), preferably washed three times each for 15 minutes using 0.5×SSC, 0.1% SDS at 42° C. (low stringency), more preferably washed three times each for 15 minutes using 0.2×SSC, 0.1% SDS at 42° C. (medium stringency), even more preferably washed three times each for 15 minutes using 0.2×SSC, 0.1% SDS at 55° C. (medium-high stringency), most preferably washed three times each for 15 minutes using 0.1×SSC, 0.1% SDS at 60° C. (high stringency), in particular washed three times each for 15 minutes using 0.1×SSC, 0.1% SDS at 68° C. (very high stringency).

Although not particularly preferred, it is contemplated that shorter probes, e.g., probes which are from about 15 to 99 nucleotides in length, such as from about 15 to about 70 nucleotides in length, may be also be used. For such short probes, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated $T_m$.

Sources for Polypeptides Having Cellobiohydrolase II Activity

A polypeptide of the present invention may be obtained from microorganisms of any genus. For purposes of the present invention, the term "obtained from" as used herein shall mean that the polypeptide encoded by the nucleotide sequence is produced by a cell in which the nucleotide sequence is naturally present or into which the nucleotide sequence has been inserted. In a preferred embodiment, the polypeptide is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may be a fungal polypeptide, and preferably a yeast polypeptide such as a *Candida, Kluyveromyces, Neocallimastix, Pichia, Piromyces, Saccharomyces, Schizosaccharomyces,* or *Yarrowia* polypeptide; or more preferably a filamentous fungal polypeptide such as an *Acremonium, Aspergillus, Chaetomium, Chaetomium, Gloeophyllum, Malbrancheae, Melanocarpus, Meripilus, Myceliophthora, Stilbella, Thielavia,* or *Trichophaea* polypeptide.

In an interesting embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In a preferred embodiment, the polypeptide is a *Chaetomium thermophilum, Myceliophthora thermophila, Acremonium thermophilum, Thielavia australiensis, Aspergilli, Thielavia microspore, Aspergillus tubingensis, Gloeophyllum trabeum, Meripilus giganteus, Trichophaea saccata, Stilbella annulata,* or *Malbrancheae cinnamomea* polypeptide It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Furthermore, such polypeptides may be identified and obtained from other sources including microorganisms isolated from nature (e.g., soil, water, plants, animals, etc.) using the above-mentioned probes. Techniques for isolating microorganisms from natural habitats are well known in the art. The nucleotide sequence may then be derived by similarly screening a genomic or cDNA library of another microorganism. Once a nucleotide sequence encoding a polypeptide has been detected with the probe(s), the sequence may be isolated or cloned by utilizing techniques which are known to those of ordinary skill in the art (see, e.g., Sambrook, Fritsch, and Maniatus, 1989, *Molecular Cloning, A Laboratory Manual*, 2d edition, Cold Spring Harbor, N.Y.).

Polypeptides encoded by nucleotide sequences of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides and Nucleotide Sequences

The present invention also relates to polynucleotides having a nucleotide sequence which encodes for a polypeptide of the invention. In particular, the present invention relates to polynucleotides consisting of a nucleotide sequence which encodes for a polypeptide of the invention. In a preferred embodiment, the nucleotide sequence is selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25. The present invention also encompasses polynucleotides comprising, preferably consisting of, nucleotide sequences which encode a polypeptide consisting of an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26, which differ from a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25 by virtue of the degeneracy of the genetic code.

The present invention also relates to polynucleotides comprising, preferably consisting of, a subsequence of a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25 which encode fragments of an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26, that have cellobiohydrolase II activity. A subsequence of a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25 is a nucleotide sequence encompassed by a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25 except that one or more nucleotides from the 5' and/or 3' end have been deleted.

The present invention also relates to polynucleotides having, preferably consisting of, a modified nucleotide sequence which comprises at least one modification in the mature polypeptide coding sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25, and where the modified nucleotide sequence encodes a polypeptide which consists of an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, and SEQ ID NO: 26.

The techniques used to isolate or clone a nucleotide sequence encoding a polypeptide are known in the art and include isolation from genomic DNA, preparation from cDNA, or a combination thereof. The cloning of the nucleotide sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other amplification procedures such as ligase chain reaction (LCR), ligated activated transcription (LAT) and nucleotide sequence-based amplification (NASBA) may be used. The nucleotide sequence may be cloned from a strain selected from a strain belonging to a genus selected from the group consisting of *Chaetomium, Myceliophthora, Melanocarpus, Acremonium, Thielavia, Aspergillus, Gloeophyllum, Meripilus, Trichophaea, Stilbella* and *Malbrancheae*, or another or related organism and thus, for example, may be an allelic or species variant of the polypeptide encoding region of the nucleotide sequence.

The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

The present invention also relates to a polynucleotide comprising, preferably consisting of, a nucleotide sequence which has a degree of identity with a nucleotide sequence selected from the group consisting of:
nucleotides 63 to 1493 of SEQ ID NO: 1,
nucleotides 1 to 246 of SEQ ID NO: 3,
nucleotides 1 to 1272 of SEQ ID NO: 3,
nucleotides 1 to 417 of SEQ ID NO: 5,
nucleotides 1 to 306 of SEQ ID NO: 7,
nucleotides 1 to 432 of SEQ ID NO: 9,
nucleotides 1 to 297 of SEQ ID NO: 11,
nucleotides 1 to 420 of SEQ ID NO: 13,
nucleotides 1 to 330 of SEQ ID NO: 15,
nucleotides 1 to 1221 of SEQ ID NO: 15,
nucleotides 1 to 429 of SEQ ID NO: 17,
nucleotides 1 to 213 of SEQ ID NO: 19,
nucleotides 43 to 701 of SEQ ID NO: 21,
nucleotides 21 to 1394 of SEQ ID NO: 23, and nucleotides 41 to 1210 of SEQ ID NO: 25 of at least 70% identity, such as at least 75% identity; preferably, the nucleotide sequence has at least 80% identity, e.g., at least 85% identity, such as at least 90% identity, more preferably at least 95% identity, such as at least 96% identity, e.g., at least 97% identity, even more preferably at least 98% identity, such as at least 99%. Preferably, the nucleotide sequence encodes a polypeptide having cellobiohydrolase II activity. The degree of identity between two nucleotide sequences is determined as described previously (see the section entitled "Definitions").

Modification of a nucleotide sequence encoding a polypeptide of the present invention may be necessary for the synthesis of a polypeptide, which comprises an amino acid sequence that has at least one substitution, deletion and/or insertion as compared to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 16, SEQ ID NO: 18, SEQ ID NO: 20, SEQ ID NO: 22, SEQ ID NO: 24, SEQ ID NO: 26 and SEQ ID NO: 28. These artificial variants may differ in some engineered way from the polypeptide isolated from its native source, e.g., variants that differ in specific activity, thermostability or pH optimum.

It will be apparent to those skilled in the art that such modifications can be made outside the regions critical to the function of the molecule and still result in an active polypeptide. Amino acid residues essential to the activity of the polypeptide encoded by the nucleotide sequence of the invention, and therefore preferably not subject to modification, such as substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for cellobiohydrolase II activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306312; Smith et al., 1992, *Journal of Molecular Biology* 224: 899904; Wlodaver et al., 1992, *FEBS Letters* 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. For a general description of nucleotide substitution, see, e.g., Ford et al., 1991, *Protein Expression and Purification* 2: 95-107.

The present invention also relates to a polynucleotide comprising, preferably consisting of, a nucleotide sequence which encodes a polypeptide having cellobiohydrolase II activity, and which hybridizes under very low stringency conditions, preferably under low stringency conditions, more preferably under medium stringency conditions, more preferably under medium-high stringency conditions, even more preferably under high stringency conditions, and most preferably under very high stringency conditions with a polynucleotide probe selected from the group consisting of (i) the complementary strand of the nucleotides selected from the group consisting of:

nucleotides 63 to 1493 of SEQ ID NO: 1,
nucleotides 1 to 246 of SEQ ID NO: 3,
nucleotides 1 to 1272 of SEQ ID NO: 3,
nucleotides 1 to 417 of SEQ ID NO: 5,
nucleotides 1 to 306 of SEQ ID NO: 7,
nucleotides 1 to 432 of SEQ ID NO: 9,
nucleotides 1 to 297 of SEQ ID NO: 11,
nucleotides 1 to 420 of SEQ ID NO: 13,
nucleotides 1 to 330 of SEQ ID NO: 15,
nucleotides 1 to 1221 of SEQ ID NO: 15,
nucleotides 1 to 429 of SEQ ID NO: 17,
nucleotides 1 to 213 of SEQ ID NO: 19,
nucleotides 43 to 701 of SEQ ID NO: 21,
nucleotides 21 to 1394 of SEQ ID NO: 23, and
nucleotides 41 to 1210 of SEQ ID NO: 25.

As will be understood, details and particulars concerning hybridization of the nucleotide sequences will be the same or analogous to the hybridization aspects discussed in the section entitled "Polypeptides Having Cellobiohydrolase II Activity" herein.

DNA Recombination (Shuffling)

The nucleotide sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25 may be used in a DNA recombination (or shuffling) process. The new polynucleotide sequences obtained in such a process may encode new polypeptides having cellobiase activity with improved properties, such as improved stability (storage stability, thermostability), improved specific activity, improved pH-optimum, and/or improved tolerance towards specific compounds.

Shuffling between two or more homologous input polynucleotides (starting-point polynucleotides) involves fragmenting the polynucleotides and recombining the fragments, to obtain output polynucleotides (i.e., polynucleotides that have been subjected to a shuffling cycle) wherein a number of nucleotide fragments are exchanged in comparison to the input polynucleotides.

DNA recombination or shuffling may be a (partially) random process in which a library of chimeric genes is generated from two or more starting genes. A number of known formats can be used to carry out this shuffling or recombination process.

The process may involve random fragmentation of parental DNA followed by reassembly by PCR to new full-length genes, e.g., as presented in U.S. Pat. Nos. 5,605,793, 5,811,238, 5,830,721, and 6,117,679. In-vitro recombination of genes may be carried out, e.g., as described in U.S. Pat. Nos. 6,159,687, 6,159,688, 5,965,408, and 6,153,510 and WO 98/41623. The recombination process may take place in vivo in a living cell, e.g., as described in WO 97/07205 and WO 98/28416.

The parental DNA may be fragmented by DNA'se I treatment or by restriction endonuclease digests as described by Kikuchi et al. (2000, *Gene* 236: 159-167). Shuffling of two parents may be done by shuffling single stranded parental DNA of the two parents as described in Kikuchi et al., (2000, *Gene* 243: 133-137).

A particular method of shuffling is to follow the methods described in Crameri et al, 1998, *Nature* 391: 288-291 and Ness et al., *Nature Biotechnology* 17: 893-896. Another format would be the methods described in U.S. Pat. No. 6,159,687: Examples 1 and 2.

Nucleic Acid Constructs

The present invention also relates to nucleic acid constructs comprising a nucleotide sequence of the present invention operably linked to one or more control sequences that direct the expression of the coding sequence in a suitable host cell under conditions compatible with the control sequences.

A nucleotide sequence encoding a polypeptide of the present invention may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising the nucleic acid construct of the invention. The various nucleotide and control sequences described above may be joined together to produce a recombinant expression vector which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169; 5771-5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al, In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a *Candida*, *Aschbyii*, *Hansenula*, *Kluyveromyces*, *Pichia*, *Saccharomyces*, *Schizosaccharomyces*, or *Yarrowia* cell.

In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium*, *Aspergillus*, *Fusarium*, *Humicola*, *Mucor*, *Myceliophthora*, *Neurospora*, *Penicillium*, *Thielavia*, *Tolypocladium*, or *Trichoderma*.

In a most preferred embodiment, the filamentous fungal host cell is an *Aspergillus awamori*, *Aspergillus foetidus*, *Aspergillus japonicus*, *Aspergillus nidulans*, *Aspergillus niger* or *Aspergillus oryzae* cell. In another most preferred embodiment, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In an even most preferred embodiment, the filamentous fungal parent cell is a *Fusarium venenatum* (*Nirenberg* sp. nov.) cell. In another most preferred embodiment, the filamentous fungal host cell is a *Humicola insolens*, *Humicola lanuginosa*, *Mucor miehei*, *Myceliophthora thermophila*, *Neurospora crassa*, *Penicillium purpurogenum*, *Thielavia terrestris*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson and Simon, editors, *Guide to Yeast Genetics and Molecular Biology, Methods in Enzymology*, 194: 182-187, Academic Press, Inc., New York; Ito et al., 1983, *Journal of Bacteriology* 153: 163; and Hinnen et al, 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide; and (b) recovering the polypeptide. Preferably, the strain is selected from a species within a genus comprised in the group consisting of *Acremonium, Aspergillus, Chaetomium, Chaetomium, Gloeophyllum, Malbrancheae, Melanocarpus, Meripilus, Myceliophthora, Stilbella, Thielavia*, or *Trichophaea*; more preferably the strain is selected from the group consisting of *Chaetomium thermophilum, Myceliophthora thermophila, Thielavia australiensis, Thielavia microspore, Aspergillus* sp., the black *Aspergilli, Aspergillus tubingensis* syn. *A. neotubingensis* Frisvad sp. nov., *Gloeophyllum trabeum, Meripilus giganteus, Trichophaea saccata, Stilbella annulata*, and *Malbrancheae cinnamomea*.

The present invention also relates to methods for producing a polypeptide of the present invention comprising (a) cultivating a host cell under conditions conducive for production of the polypeptide; and (b) recovering the polypeptide.

The present invention also relates to methods for in-situ production of a polypeptide of the present invention comprising (a) cultivating a host cell under conditions conducive for production of the polypeptide; and (b) contacting the polypeptide with a desired substrate, such as a cellulosic substrate, without prior recovery of the polypeptide. The term "in-situ production" is intended to mean that the polypeptide is produced directly in the locus in which it is intended to be used, such as in a fermentation process for production of ethanol.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989).

Plants

The present invention also relates to a transgenic plant, plant part, or plant cell which has been transformed with a nucleotide sequence encoding a polypeptide having cellobiohydrolase II activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an anti-nutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, millets, and maize (corn).

Examples of dicot plants are tobacco, lupins, potato, sugar beet, legumes, such as pea, bean and soybean, and cruciferous plants (family Brassicaceae), such as cauliflower, rape, canola, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny (clonal or seed) of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleotide sequence encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285-294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleotide sequence encoding a polypeptide having cellobiohydrolase II activity of the present invention under conditions conducive for production of the polypeptide; and (b) recovering the polypeptide.

The present invention also relates to methods for in-situ production of a polypeptide of the present invention comprising (a) cultivating a transgenic plant or a plant cell comprising a nucleotide sequence encoding a polypeptide having cellobiohydrolase II activity of the present invention under conditions conducive for production of the polypeptide; and (b) contacting the polypeptide with a desired substrate, such as a cellulosic substrate, without prior recovery of the polypeptide.

Compositions

In a still further aspect, the present invention relates to compositions comprising a polypeptide of the present invention.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Detergent Compositions

The polypeptide of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the polypeptide of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas lipase*, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus lipase*, e.g., from *B. subtilis* (Dartois et al., 1993, *Biochemica et Biophysica Acta* 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Amylases: Suitable amylases (alpha and/or beta) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, and 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, and WO 98/08940. Other examples are cellulase variants such as those described in WO 94/07998, EP 0 531 315, U.S. Pat. Nos. 5,457,046, 5,686,593, and 5,763,254, WO 95/24471, WO 98/12307 and PCT/DK98/00299.

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the polypeptide of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The polypeptide of the invention may additionally be incorporated in the detergent formulations disclosed in WO 97/07202 which is hereby incorporated as reference.

Production of Ethanol from Biomass

The present invention also relates to methods for producing ethanol from biomass, such as cellulosic materials, comprising contacting the biomass with the polypeptides of the invention. Ethanol may subsequently be recovered. The polypeptides of the invention may be produced "in-situ", i.e., as part of, or directly in an ethanol production process, by cultivating a host cell or a strain, which in its wild-type form is capable of producing the polypeptides, under conditions conducive for production of the polypeptides.

Ethanol can be produced by enzymatic degradation of biomass and conversion of the released polysaccharides to ethanol. This kind of ethanol is often referred to as bioethanol or biofuel. It can be used as a fuel additive or extender in blends of from less than 1% and up to 100% (a fuel substitute). In some countries, such as Brazil, ethanol is substituting gasoline to a very large extent.

The predominant polysaccharide in the primary cell wall of biomass is cellulose, the second most abundant is hemi-cellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Three major classes of cellulase enzymes are used to breakdown biomass:

The "endo-1,4-beta-glucanases" or 1,4-beta-D-glucan-4-glucanohydrolases (EC 3.2.1.4), which act randomly on soluble and insoluble 1,4-beta-glucan substrates.

The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and 1,4-beta-D-glucan cellobiohydrolase (EC 3.2.1.91), also referred to as cellobiohydrolase I and II, which liberates D-cellobiose from 1,4-beta-glucans.

The "beta-D-glucosidases" or beta-D-glucoside glucohydrolases (EC 3.2.1.21), which act to release D-glucose units from cellobiose and soluble cellodextrins, as well as an array of glycosides.

These three classes of enzymes work together synergistically in a complex interplay that results in efficient decrystallization and hydrolysis of native cellulose from biomass to yield the reducing sugars which are converted to ethanol by fermentation.

The present invention is further described by the following examples which should not be construed as limiting the scope of the invention.

EXAMPLES

Chemicals used as buffers and substrates were commercial products of at least reagent grade.

Example 1

Molecular Screening of Cellobiohydrase II from Thermophilic Fungi

The fungal strains were grown in 80 ml liquid media (2.5% Avicel, 0.5% Glucose, 0.14% $(NH_4)_2SO_4$) in 500 ml Erlenmeyer flasks. The flasks were incubated for 72 hours at 45° C. on a rotary shaker at 165 rpm. Mycelium was harvested by centrifugation at 7000 rpm for 30 minutes and stored at −80° C. before use for RNA extraction.

Total RNA was extracted from 100 mg mycelium of each strain using the RNeasy Mini Kit (QIAGEN, Cat. No. 74904).

Degenerate primers were designed based on alignment of already known CBHII protein sequences. The following primers were designed (see also SEQ ID NOS: 27 to 32).

```
                                        SEQ ID NO: 27
CBHII 1S:    5' TGG GGN CA(A/G) TG(T/C) GGN GG 3'

SEQ ID NO: 28
CBHII 2S:    5' TGG (T/C)TN GGN TGG CCN GC 3'

SEQ ID NO: 29
CBHII 2AS:   5' GCN GGC CAN CCN A(A/G)C CA 3'
             (reverse)

SEQ ID NO: 30
CBHII 3AS:   5' TT(A/G) CAC CA(A/G) TCN CCC CA 3'
             (reverse)

SEQ ID NO: 31
CBHII 4AS:   5' GG(T/C) TTN ACC CAN AC(A/G) AA 3'
             (reverse)

SEQ ID NO: 32
CBHII 5AS:   5' AA(A/G) TAN GC(T/C) TG(A/G) AAC CA
             3' (reverse)
```

The 3' RACE system (GIBCO., Cat. No. 18373-019) were used to synthesize cDNA from total RNA. About 5 micrograms total RNA was used as template and Adapter Primer (provided by 3'RACE system) was used to synthesize the first strand of cDNA. Then cDNA was amplified by using different combinations of degenerate primers. The reaction mixture comprised 2.5 microL 10×PCR buffer, 1.5 microL 25 mM $MgCl_2$, 1.5 microL 25 mM $MgCl_2$, 0.5 microL 10 mM dNTP mix, 0.5 microL, 10 microM 3' Primer, 0.5 microL AUAP (10 microM, provided by 3' RACE system), 0.5 microL TaqDNA polymerase (5 u/microL, Promega), 1 microL cDNA synthesis reaction and autoclaved, distilled water to 25 microL.

PCR was performed under the following conditions: The reaction was submitted to 94° C. for 3 minutes followed by 30 cycles of 94° C. for 30 sec, 50° C. for 30 sec and extension at 72° C. for 1 minute. A final extension step at 72° C. for 10 minutes followed by a 4° C. hold step completed the program.

PCR products of the right size for each pair of primer were recovered from 1% agarose (1×TBE) gel, then purified by incubation in a 60° C. water bath followed by purification using GFXTMPCR DNA and Gel Band Purification Kit. (Amersham Pharmacia Biotech Inc., Cat. No. 27-9602-01). The concentrations of purified products were determined by measuring the absorbance of A260 and A280 in a spectrophotometer. Then these purified fragments were ligated to pGEM-T Vector (Promega, Cat. No. A3600) according to the kit from Promega (Cat. No. A3600).

Using the "heat shock" method I microL ligation products were transformed into 50 microL JM109 high efficiency competent cells. Transformation cultures were plated onto LB plates with ampicillin/IPTG/X-Gal, and plates were incubated overnight at 37° C. Recombinant clones were identified by color screening on indicator plates and colony PCR screening. The positive clones were inoculated into 3 ml LB liquid medium and incubate overnight at 37° C. on a rotary shaker at 250 rpm. The cells were pelleted by centrifugation for 5 min at 10,000×g and plasmid sample were prepared from the cell pellet by using Minipreps DNA Purification System (Promega, Cat. No. A7100). Finally the plasmids were sequenced with BigDye Terminator Cycle Sequencing Ready Reaction Kit (PE) by using ABI377 sequencer. The sequencing reaction was as follows: 4 microL Terminator Ready Reaction Mix, 1.0-1.5 microgram Plasmid DNA, 3.2 pmol Primer and $dH_2O$ to a final volume of 10 microL.

Sequence analysis of the cDNA clones from different primer pairs showed that the sequences contain coding regions of CBHII gene. The primers were successfully used for molecular screening of CBHII gene from all tested fungal species within *Chaetomium thermophilum, Myceliophtora thermophila, Acremonium thermophilum, Melanocarpus* sp., *Thielavia microspore, Aspergillus* sp., *Thielavia australiensis, Aspergillus tubingensis, Gloeophyllum trabeum, Meripilus giganteus, Trichophaea saccata, Stibella anualata* and *Malbrancheae cinnamonea*. The identified CBH II encoding DNA sequences are shown as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25. Full-length sequences were obtained from *Aspergillus tubingensis, Chaetomium thermophilum, Myceliophtora thermophila, Trichophaea saccata, Stibella anualata,* and *Malbrancheae cinnamonea*. From *Acremonium thermophilum, Melanocarpus* sp., *Thielavia microspore, Aspergillus* sp., *Thielavia australiensis, Gloeophyllum trabeum* and *Meripilus giganteus* only partial sequences have been obtained.

Alternatively to the method applied above, the cDNA library could be screened for the full-length cDNA using standard hybridization techniques and the partial cDNA sequence as a probe. The clones giving a positive hybridization signal with the probe are then purified and sequenced to determine the longest cDNA sequence. Homology search and comparison confirms that the full-length cDNA correspond to the partial CBH II cDNA sequence that was originally used as a probe.

The two approaches described above rely on the presence of the full-length CBH II cDNA in the cDNA library or in the cDNAs used for its construction. Alternatively, the 5' and 3' RACE (Rapid Amplification of cDNA Ends) techniques or derived techniques could be used to identify the missing 5' and 3' regions. For this purpose, mRNAs from are isolated and utilized to synthesize first strand cDNAs using oligo(dT)-containing Adapter Primer or a 5'-Gene Specific Primer (GSP).

The full-length cDNA of the CBH II gene can also be obtained by using genomic DNA. The CBH II gene can be identified by PCR techniques such as the one describe above or by standard genomic library screening using hybridization techniques and the partial CBH II cDNA as a probe. Homology search and comparison with the partial CBH II cDNA is used to that the genomic sequence correspond to the CBH II gene. Identification of consensus sequences such as initiation site of transcription, start and stop codons or polyA sites could be used to define the region comprising the full-length cDNA. Primers constructed from both the 5' and 3' ends of this region could then be used to amplify the full-length cDNA from mRNA or cDNA library (see above).

By expression of the full-length gene in a suitable expression host construct the CBH II enzyme is harvested as an intra cellular or extra cellular enzyme from the culture broth.

Example 2

Using Blast the protein sequences were compared to SWall, ERDBP, and GenSeqP. If the sequenced was full length, the catalytic core was predicted using PFAMM HMM and only that core region was used to search the databases. The highest hit to the public databases are listed except where the sequence is a duplicate to a sequence already present in the ERDB.

*Chaetomium thermophilum* NP000980 has 83% identity to the *Humicola insolens* avicelase II Glycosyl hydrolase in SWALL:Q9C1S9, family 6 domain.

*Myceliophtora thermophila* NP001130 has 79% protein identity to the *H. insolens* NCE2 in geneseqp|aaw44827|aaw44827.

*Acremonium* sp. T178-4 NP001132 has 74% protein identity to the *Acremonium cellulolyticus* cellulase geneseqp|aaw25789|aaw25789. Glycosyl hydrolase family 6 domain.

*Melanocarpus* sp. AT181-3 NP001133 has 91% protein identity to the *H. insolens* Cel6A fungal cellulase in geneseqp|aaw01077|aaw01077. Glycosyl hydrolase family 6 domain.

*Thielavia microspora* T046-1 NP001134 has 79% protein identity to the *H. insolens* cellulase NC2 in geneseqp|aaw44827|aaw44827. Glycosyl hydrolase family 6 domain.

*Aspergillus* sp. T1882 NP001136 has 71% protein identity to the exocellobiohydrolase in geneseqp|aaw02321|aaw02321 *Phanerochaete chrysosporium*. Glycosyl hydrolase family 6 domain.

*Thielavia australiensis* NP001000 has 77% protein identity to the *H. insolens* cellulase NC2 protein in geneseqp|aaw44827|aaw44827. Glycosyl hydrolase family 6 domain.

*Aspergillus tubingensis* NP001143 has 67% protein identity to the CBHII in SWALL:Q8NIB5 *Talaromyces emersonii*. The DNA sequence entry is 94% identical to NP001144 *Gloeophyllum trabeum*. Glycosyl hydrolase family 6 domain.

*Gloeophyllum trabeum* NP001144 67% protein identity to the CBHII SWALL:Q8NIB5 *Talaromyces emersonii*. The DNA sequence entry is 94% identical to NP001144 *Gloeophyllum trabeum*.

Example 3

Sequencing of the *Malbranchia cinnamonea* CBH II Gene and the *Stilbella anulata* CBH II Gene The cDNA inserts in plasmids Clone ZY043193, a cDNA encoding the *Malbranchia cinnamonea* CBH II, and clone ZY040206, a cDNA encoding the *Stilbella anulata* CBH II, were sequenced to phred quality values >40, indicating high confidence DNA sequence data. DNA sequencing was performed on an ABI 3700 (ABI, Foster City, Calif.) according to the manufacturer's protocols. Assembly of sequence data was performed using phred/phrap/consed (University of Washington).

Example 4

Construction of Expression Plasmids for the *Malbranchia cinnamonea* CBH II Gene and the *Stilbella anulata* CBH II Gene The clone and the nucleotide sequences of the *Malbranchia cinnamonea* CBH II gene described above are used for subcloning of the gene and expression in *Aspergillus* host. Polymerase chain reaction approach is used to subclone the CBHII gene (without its own promoter) from the isolated cDNA clone ZY043193 using primers designed from the nucleotide sequences. In order to facilitate the subcloning of the gene fragment into the pAILo 2 expression vector, BspHI and Pac I restriction enzyme sites, respectively, at the 5' and 3' end of the gene, are introduced. The vector pAILo 2 contains the TAKA promoter, NA2-tpi leader and AMG terminator as regulatory sequences. The plasmid also contains *Aspergillus nidulans* pyrG gene as a selectable marker for fungal transformations. The following primers are used for PCR amplification process:

```
                                       (SEQ ID NO: 33)
Primer F4 (forward):
5' GGGTCATGAGAGACTCTTTGTTCAC 3'

(SEQ ID NO: 34)
Primer R4 (reverse):
5' GGGTTAATTAATTAGAATGGGGGGTTGGCATTTC 3'
```

PCR is performed using Pwo polymerase (Boehringer Mannheim) according to the manufacturers specifications. The PCR amplified product is gel isolated and cut with BspH I and Pac I enzymes and gel purified. The purified fragment is ligated to a pAILo 2 vector (already cut with Nco I and Pac I) to get the plasmid pEJG100 in which the transcription of the *M. cinnamonea* CBH II gene is under the control of the TAKA promoter. The plasmid, pEJG100, is transformed into *E. coli* Solopac Gold cells (Stratagene, La Jolla, Calif.) cells. *E. coli* transformants containing the pEJG100 plasmid are isolated and plasmid DNA is prepared for transformation and expression in *Aspergillus*.

The clone and the nucleotide sequences of the *Stilbella anulata* CBH II gene described above are used for subcloning of the gene and expression in an *Aspergillus* host. Polymerase chain reaction approach is used to subclone the CBHII gene (without its own promoter) from the isolated cDNA clone ZY040206 using primers designed from the nucleotide sequences. In order to facilitate the subcloning of the gene fragment into the pALLO2 expression vector, PCR primers were designed containing restriction sites compatible to the cloning sites of pALLO2 (NcoI and PacI) and to satisfy overlap requirements for the Infusion PCR kit protocol (Clonetech, Palo Alto, Calif.). The following primers are used for PCR amplification process:

```
                                       (SEQ ID NO: 35)
Primer F4.1 (forward):
5' ACTGGATTTACCATGGCCGGTCGATTCTTCC 3'

(SEQ ID NO: 36)
Primer R4.1 (reverse):
5' AGTCACCTCTAGTTATTAGAAGGCGGGGTTG 3'
```

The PCR product was generated using Pfx enzyme (Life Technologies) with 1× enhancer. The 1400 bp product was gel excised, purified with Qiaquick (Qiagen, Valencia, Calif.), ligated into pALLO2 with the Infusion reaction. The resulting plasmid, pEJG96, is transformed into *E. coli* Solopac Gold cells (Stratagene, La Jolla, Calif.). *E. coli* transformants containing the pEJG96 plasmid are isolated and plasmid DNA is prepared for transformation and expression in *Aspergillus*.

Example 5

Transformation of *Aspergillus oryzae*

Protoplasts are prepared from *A. oryzae* strain JAL 250 in which the pyrG gene of the host strain is deleted. Protoplast preparation and transformation are done as previously described (Christensen et al., supra). *A. oryzae* transformants expressing orotidine monophosphate decarboxylase are selected based on their ability to grow in the absence of uracil, Transformants are, spore purified twice on selective plates and the spore purified transformants used for further analysis.

Example 6

Expression of *Malbranchia cinnamonea* CBH II Gene and the *Stilbella anulata* CBH II Gene in *A. oryzae*

The transformants are screened for CBH II expression in shake flasks (25 ml medium in 125 ml flasks) using a medium that contains the following in g/L: maltose 50; $MgSO_4.7H_2O$, 2.0; $KH_2PO_4$, 10.0; $K_2SO_4$, 2.0; citric acid, 2.0; yeast extract, 10.0; AMG trace metal solution, 0.5 ml; urea 2.0. The pH of the medium is adjusted to 6.5 before sterilization by autoclaving. Flasks are inoculated with freshly harvested spores and incubated in a shaker (200 rpm) at 34° C. Culture supernatants are harvested at 5 days. Five microliters of the culture supernatant is run on 8-16% Tris-Glycine gels. For the *Malbranchia cinnamonea* CBH II, the predicted molecular weight of the protein is 43 kDa. A smear, significant over background, runs at about 50 kDa is seen in the transformants. For the *Stilbella anulata* CBH II, the predicted molecular weight of the protein is 49 kDa. A band, significant over background, runs at about 55 kDa in the transformant.

Example 7

The phosphoric acid cellulose (PASC) was prepared as described by Schulein, 1997, *J. Biotechnol*. 57: 71-81. Protein concentrations were determined using a BCA Protein Assay (Pierce) as per the manufacturer's instructions. Protein aliquots were examined on 8-16% Acrylamide gradient gels (Invitrogen) and stained with Biosafe Coomassie Stain (Biorad).

*Aspergillus oryzae* broths expressing the *Stilbella annulata* Cel6A (~55 kD) and the *Malbranchia cinnamonea* Cel6A (~49 kD) enzymes were concentrated using Centricon Plus 20 (Millipore) filtering devices using a swinging bucket rotor centrifuge (Sorvall RC3B Plus; total time of ~25 minutes at 3000 rpm). Approximately 3 ml of each concentrate was loaded onto a 10DG Econo PAC column (Biorad) equilibrated with 50 mM sodium acetate pH 5.0 and the desalted material eluted with 4 ml of 50 mM sodium acetate, pH 5.0. The protein concentrations for each sample were determined and aliquots analyzed on 8-16% Acrylamide gradient gels. A PASC activity assay (endpoint assay) was performed utilizing a 96 well microplate format. Briefly, 10 microL of appropriately diluted glucose standards (2 mg/ml to 0.25 mg/ml) were placed in wells containing 190 microL of 50 mM sodium acetate buffer pH 5.0 and 0.5 mg/ml BSA (Dilution buffer). Reagent controls (200 microL Dilution buffer), Sample controls (10 microL dilution to be assayed plus 190 microL Dilution buffer) and Substrate controls (10 microL Dilution buffer plus 190 microL 2 g/L PASC in Dilution buffer) were included in each assay. A set of serial dilutions were generated for each sample to be assayed and 10 microL of each dilution placed in their designated wells. Reactions were initiated by the addition of 190 microL of 2 g/L PASC. Samples were mixed and the plates placed in a 50° C. water bath for 30 minutes. The reactions were stopped by the addition of 500 microL of 0.5 M NaOH to each well. Plates were centrifuged (Sorvall RT7) for 5 minutes at 2000 rpm and 100 microL aliquots of each sample transferred to a 96 well microtiter plate with conical wells. Determination of reducing sugar content was initiated by adding 50 microL of 1.5% (w/v) p-Hydroxybenzoic Acid Hydrazide (PHBAH) to each well and incubating the plate at 95° C. for 10 minutes. The plate was allowed to cool to room temperature and 50 microL of double distilled $H_2O$ added to each well. At this time 100 microL aliquots from each well were transferred to a flat bottomed 96 well microtiter plate and the OD 410 read using a Spectra MAX plate reader.

The glucose standards prepared for the PHBAH portion of the assay were used to construct a glucose standard curve (A410 vs Glucose concentration in mg/ml). The slope and intercept from this standard curve was used to generate a second graph in which the micromoles reducing sugar/min/ml was plotted vs protein concentration (mg/ml) to give the specific activities (IU/mg) of the samples assayed at 50° C. The specific activity for Stilbella annulata was 0.24 (IU/mg) and for Malbranchia cinnamonea 1.40 (IU/mg).

Example 8

Cellobiohydrolase Activity

A cellobiohydrolase is characterized by the ability to hydrolyze highly crystalline cellulose very efficiently compared to other cellulases. Cellobiohydrolase may have a higher catalytic activity using PASC (phosphoric acid swollen cellulose) as substrate than using CMC as substrate. For the purposes of the present invention, any of the following assays can be used to identify cellobiohydrolase activity:

Activity on Azo-Avicel

Azo-Avicel (Megazyme, Bray Business Park, Bray, Wicklow, Ireland) was used according to the manufacturer's instructions.

Activity on PNP-Beta-Cellobiose 50 microL CBH substrate solution (5 mM PNP beta-D-Cellobiose (p-Nitrophenyl β-d-Cellobioside Sigma N-5759) in 0.1 M Na-acetate buffer, pH 5.0) was mixed with 1 mL substrate solution and incubated 20 minutes at 40° C. The reaction was stopped by addition of 5 mL stop reagent (0.1 M Na-carbonate, pH 11.5). Absorbance was measured at 404 nm.

Activity on PASC and CMC

The substrate is degraded with cellobiohydrolase to form reducing sugars. A Microdochium nivale carbohydrate oxidase (rMnO) or another equivalent oxidase acts on the reducing sugars to form $H_2O_2$ in the presence of $O_2$. The formed $H_2O_2$ activates in the presence of excess peroxidase the oxidative condensation of 4-aminoantipyrine (AA) and N-ethyl-N-sulfopropyl-m-toluidine (TOPS) to form a purple product which can be quantified by its absorbance at 550 nm.

When all components except cellobiohydrolase are in surplus, the rate of increase in absorbance is proportional to the cellobiohydrolase activity. The reaction is a one-kinetic-step reaction and may be carried out automatically in a Cobas Fara centrifugal analyzer (Hoffmann La Roche) or another equivalent spectrophotometer which can measure steady state kinetics.

Buffer: 50 mM Na-acetate buffer (pH 5.0);

Reagents: rMnO oxidase, purified Microdochium nivale carbohydrate oxidase, 2 mg/L
 Peroxidase, SIGMA P-8125 (96 U/mg), 25 mg/L
 4-aminoantipyrine, SIGMA A-4382, 200 mg/L
 TOPS, SIGMA E-8506, 600 mg/L
 PASC or CMC (see below), 5 g/L
 All reagents were added to the buffer in the concentrations indicated above and this reagent solution was mixed thoroughly.

50 microL cellobiohydrolase II sample (in a suitable dilution) was mixed with 300 microL reagent solution and incubated 20 minutes at 40° C. Purple color formation was detected and measured as absorbance at 550 nm.

The AA/TOPS-condensate absorption coefficient is 0.01935 $A_{550}$/(microM cm). The rate is calculated as micromoles reducing sugar produced per minute from $OD_{550}$/minute and the absorption coefficient.

PASC:

Materials: 5 g Avicel® (Art. 2331 Merck);
 150 mL 85% Ortho-phosphoric-acid (Art. 573 Merck);
 800 mL Acetone (Art. 14 Merck);
 Approx. 2 liters deionized water (Milli-Q);
 1 L glass beaker;
 1 L glass filter funnel;
 2 L suction flask;
 Ultra Turrax Homogenizer.

Acetone and ortho-phosphoric-acid is cooled on ice. Avicel® is moisted with water, and then the 150 mL icecold 85% Orthophosphoric-acid is added. The mixture is placed on an icebath with weak stirring for one hour.

Add 500 mL ice-cold acetone with stirring, and transfer the mixture to a glass filter funnel and wash with 3×100 mL ice-cold acetone, suck as dry as possible in each wash. Wash with 2×500 mL water (or until there is no odor of acetone), suck as dry as possible in each wash.

Re-suspend the solids in water to a total volume of 500 mL, and blend to homogeneity using an Ultra Turrax Homogenizer. Store wet in refrigerator and equilibrate with buffer by centrifugation and re-suspension before use.

CMC:

Bacterial cellulose microfibrils in an impure form were obtained from the Japanese foodstuff "nata de coco" (Fujico Company, Japan). The cellulose in 350 g of this product was purified by suspension of the product in about 4 L of tap water. This water was replaced by fresh water twice a day for 4 days.

Then 1% (w/v) NaOH was used instead of water and the product was re-suspended in the alkali solution twice a day for 4 days. Neutralization was done by rinsing the purified cellulose with distilled water until the pH at the surface of the product was neutral (pH 7).

The cellulose was microfibrillated and a suspension of individual bacterial cellulose microfibrils was obtained by homogenization of the purified cellulose microfibrils in a Waring blender for 30 min. The cellulose microfibrils were further purified by dialyzing this suspension through a pore membrane against distilled water and the isolated and purified cellulose microfibrils were stored in a water suspension at 4° C.

Example 9

Expression of Malbranchia Cinnamonea CBH II Gene in *A. oryzae*

The *Malbranchia cinnamonea* CBH II gene was expressed in *Aspergillus oryzae* and an enzyme of approximately 42 kDa was purified to a purity of 95%. The activity was 1650 pnp-BDG.

Example 10

Two recombinantly expressed (*Aspergillus oryzae*) CBHII enzymes from *Stilbella annulata* (Cel6A) and *Malbranchea cinnamonea* (Cel6B) were assayed for enzymatic activity on phosphoric acid cellulose (PASC).

*Aspergillus oryzae* broths expressing recombinant *Stilbella annulata* Cel6A (~55 kDa) and the *Malbranchia cinnamonea* Cel6B (~49 kDa) were concentrated using Centricon Plus 20 filtering devices using a swinging bucket rotor (Sorvall RC3B Plus; ~25 minutes at 3,000 rpm). Approximately 3 ml of each concentrate was loaded onto a 10DG Econo PAC column (Biorad) equilibrated with 50 mM sodium acetate pH 5.0 and the desalted material eluted with 4 ml of 50 mM sodium acetate pH 5.0. The protein concentrations for each sample were determined using a BCA Protein Assay Kit (Pierce) and aliquots analyzed on 8-16% Acrylamide gradient gels (Invitrogen).

A PASC activity assay was performed utilizing a 96 well microplate format. Briefly, 10 microL of an appropriate glucose standard (2 mg/ml to 0.25 mg/ml) was placed in a well containing 190 microL of 50 mM sodium acetate buffer pH 5.0 and 0.5 mg/ml BSA (Dilution buffer). Reagent controls (200 microL dilution buffer), sample controls (10 microL dilution to be assayed plus 190 microL dilution buffer) and substrate controls (10 microL dilution buffer plus 190 microL 2 g/L PASC in dilution buffer) were also run. A series of serial dilutions were set up for each sample and 10 microL of each dilution placed in their designated wells. Reactions were initiated by adding 190 microL of 2 g/L PASC. Plates were covered and placed in a 50° C. water bath for 30 minutes. Reactions were stopped by the addition of 500 microL of 0.5 M NaOH to each well. Plates were centrifuged (Sorvall RT7) for 5 minutes at 2000 rpm. Approximately 100 microL aliquots of each sample were transferred to a 96 well microtiter plate with conical wells. Each well then received 50 microL of 1.5% p-Hydroxybenzoic Acid Hydrazide (PHBAH) and was mixed thoroughly. Plates were incubated at 95° C. for 10 minutes. Following the incubation step plates were cooled to room temperature and 50 microL of ddH$_2$O added to each well. One hundred microL aliquots from each well were transferred to flat bottomed 96 well microtiter plates and the OD 410 nm read using a Spectra MAX plate reader.

Using the glucose standard curve (A410 vs Glucose in mg/ml) generated for the PASC assay the slope and intercept from this curve was used to construct a second graph in which the umoles reducing sugar/min/ml was plotted vs protein concentration (mg/ml) to give the specific activities (IU/mg) for the enzyme samples assayed. In determining specific activity (SA) on PASC only percent conversions of less than 2% were used.

Hydrolysis of PCS was conducted using 1.1 ml Immunoware microtubes (Pierce) using a total reaction volume of 1.0 ml. In this protocol hydrolysis of PCS (20 mg/ml in 50 mM sodium acetate pH 5.0 buffer) was performed using different protein loadings (expressed as mg Enzyme per gram PCS) of a *Thielavia terrestris* broth or Celluclast 1.5 L sample in the presence of 3% *Aspergillus oryzae* beta glucosidase (3% of Cellulase protein loading). Characterization of *Thielavia*'s PCS hydrolyzing capability was done at multiple temperatures: 40° C., 50° C. and 65° C. (Isotemp 102S water baths). Typically, reactions were run in duplicate and aliquots taken during the course of hydrolysis (t=0, 2, 4, 6, 8 and 24 hours). PCS hydrolysis reactions were stopped by mixing a 20 microL aliquot of each hydrolyzate with 180 microL of 0.44% NaOH (Stop reagent). Appropriate serial dilutions were generated for each sample and the reducing sugar content determined using a p-Hydroxybenzoic Acid Hydrazide (PHBAH) assay adapted to a 96 well microplate format. Briefly, a 90 microL aliquot of an appropriately diluted sample was placed in a 96 well conical bottomed microplate. Reactions were initiated by adding 60 microL of 1.5% (w/v) PHBAH in 2% NaOH to each well. Plates were heated uncovered at 95° C. for 10 minutes. Plates were allowed to cool to RT and 50 microL of ddH$_2$O added to each well. A 100 microL aliquot from each well was transferred to a flat bottomed 96 well plate and the absorbance at A410 nm measured using a SpectraMax Microplate Reader (Molecular Devices). Glucose standards (0.1-0.0125 mg/ml diluted with 0.4% sodium hydroxide) were used to prepare a standard curve to translate the obtained A410 values into glucose equivalents. The resultant equivalents were used to calculate the percentage of PCS cellulose conversion for each reaction. Our benchmark conditions for Celluclast 1.5 L PCS hydrolysis was the following: 50 mg/ml PCS in 50 mM sodium acetate pH 5.0, ~21 mg Enzyme/g PCS (Equal to ~10 FPU), in the absence of externally added beta glucosidase at 38° C.

*Aspergillus oryzae* broths expressing the CBHII enzymes from *Stilbella annulata* (Cel6A) and *Malbranchea cinnamonea* (Cel6B) were desalted, concentrated and their protein concentrations determined as described in the materials and methods. Analysis of these recombinant protein samples on a 8-16% Acrylamide gradient gel indicates the *Stilbella* Cel6A enzyme (FIG. 1, lane #1) has an apparent molecular weight of ~55° kDa while that of *Malbranchea* Cel6B is ~49 kDa (FIG. 1, lane #2).

To determine whether or not these recombinant enzymes were enzymatically active hydrolysis reactions were conducted using a PASC substrate. Under the conditions described previously *Stilbella annulata* (Cel6A) and *Malbranchea cinnamonea* (Cel6B) had specific activities of 0.24 IU/mg and 1.40 IU/mg, respectively.

DEPOSIT OF BIOLOGICAL MATERIAL

China General Microbiological Culture Collection Center (CGMCC)

The following biological material has been deposited Dec. 19, 2002 under the terms of the Budapest Treaty with the China General Microbiological Culture Collection Center (CGMCC), Institute of Microbiology, Chinese Academy of Sciences, Haidian, Beijing 100080, China:

Accession Number: CGMCC 0859
Applicants' reference: NP000980
Description: *Chaetomium thermophilum*
Classification: Chaetomiaceae, Sordariales, Ascomycota
Related sequence(s): SEQ ID NO: 1, SEQ ID NO: 2
Accession Number: CGMCC 0862
Applicants' reference: NP 001130
Description: *Myceliophthora thermophila*
Classification: Chaetomiaceae, Sordariales, Ascomycota
Related sequence(s): SEQ ID NO: 3, SEQ ID NO: 4
Accession Number: *Acremonium* sp. T178-4 CGMCC 0857
Applicants' reference: NP001132
Description: *Acremonium* sp. T178-4
Classification: mitosporic Ascomycetes
Related sequence(s): SEQ ID NO: 5, SEQ ID NO: 6
Accession Number: *Melanocarpus* sp. CGMCC 0861
Applicants' reference: NP001133
Description: *Melanocarpus* sp.
Classification: Trichocomaceae, Eurotiales, Ascomycota
Related sequence(s): SEQ ID NO: 7, SEQ ID NO: 8
Accession Number *Thielavia microspora* CGMCC 0863
Applicants' reference: NP001134
Description: *Thielavia microspora*
Classification: Chaetomiaceae, Soradariales, Ascomycota
Related sequence(s): SEQ ID NO: 9, SEQ ID NO: 10
Accession Number: *Aspergillus* sp. T186-2 CGMCC 0858
Applicants' reference: NP001132
Description: *Aspergillus* sp. T186-2
Classification: Trichocomaceae, Eurotiales, Ascomycota
Related sequence(s): SEQ ID NO: 11, SEQ ID NO: 12
Accession Number: *Thielavia austfaliensis* CGMCC 0864
Applicants' reference: NP001000
Description: *Thielavia australiensis*
Classification: Chaetomiaceae, Sordariales, Ascomycota
Related sequence(s): SEQ ID NO: 13, SEQ ID NO: 14
American Type Culture Collection (ATCC)

The following biological material is obtainable from American Type Culture Collection, P.O. Box 1549, Manassas, Va. 20108, USA.

Accession Number: ATCC 11.39
Applicants reference: NP001144
Description: *Gloeophyllum trabeum*
Classification: -
Related sequence(s): SEQ ID NO: 17, SEQ ID NO: 18

Centraalbureau Voor Schimmelcultures (CBS)
The following biological material is obtainable from Centraalbureau Voor Schimmelcultures (CBS), Uppsalalaan 8, 3584 CT Utrecht, The Netherlands (alternatively P.O. Box 85167, 3508 AD Utrecht, The Netherlands):

Accession Number: CBS 161.79
Applicants' reference: NP001143
Description: *Aspergillus tubingensis*
Classification: -
Related sequence(s): SEQ ID NO: 15, SEQ ID NO: 16
Accession Number: CBS 521.95
Applicants' reference: ND001631
Description: *Meripilus giganteus*
Classification: -
Related sequence(s): SEQ ID NO: 19, SEQ ID NO: 20
Accession Number: CBS 804.70
Applicants' reference: NP000960
Description: *Trichophaea saccata*
Classification: -
Related sequence(s): SEQ ID NO: 21, SEQ ID NO: 22
Accession Number: CBS 185.70
Applicants' reference: NP001040
Description: *Stilbella annulata*
Classification: -
Related sequence(s): SEQ ID NO: 23, SEQ ID NO: 24
Accession Number: CBS 115.68
Applicants' reference: NP 001045
Description: *Malbranchea cinnamomea*
Classification: -
Related sequence(s): SEQ ID NO: 25, SEQ ID NO: 26

The invention claimed is:

1. An isolated polypeptide having cellobiohydrolase II activity, selected from the group consisting of:
   (a) a polypeptide having an amino acid sequence comprising the amino acid sequence shown as amino acids 1 to 82 of SEQ ID NO:4, and a polypeptide having an amino acid sequence comprising at least 85% identity with the amino acid sequence shown as amino acids 1 to 420 of SEQ ID NO: 4;
   (b) a polypeptide having an amino acid sequence which is encoded by nucleotides 1 to 246 of SEQ ID NO: 3 and nucleotides 1 to 1272 of SEQ ID NO: 3;
   (c) a polypeptide which is encoded by a nucleotide sequence which hybridizes under high stringency conditions with a polynucleotide probe selected from the group consisting of: (i) the full complementary strand of the nucleotides selected from the group consisting of: nucleotides 1 to 246 of SEQ ID NO: 3, and nucleotides 1 to 1272 of SEQ ID NO: 3; and (ii) the full complementary strand of the nucleotides selected from the group consisting of: nucleotides 1 to 200 of SEQ ID NO: 3, and nucleotides 1 to 1272 of SEQ ID NO: 3; and
   (d) a fragment of (a), (b) or (c) that has cellobiohydrolase II activity,
   wherein said high stringency hybridization of the nucleotide sequence is at 42° C. in 5×SSPE, 1.0% SDS, 5×Denhardt's solution, 100 micro gram/ml denatured salmon sperm DNA, and followed by washing three times each for 15 minutes using 0.1×SSC, 0.1% SDS at 60° C.

2. The polypeptide of claim 1, comprising an amino acid sequence selected from the group consisting of:
   a polypeptide having an amino acid sequence selected from the group consisting of: an amino acid sequence comprising the amino acid sequence shown as amino acids 1 to 82 of SEQ ID NO: 4, and a polypeptide having an amino acid sequence which has at least 90% identity with the amino acid sequence shown as amino acids 1 to 420 of SEQ ID NO: 4.

3. The polypeptide of claim 1, where the polypeptide is a variant which comprises an amino acid sequence that has at least one substitution, deletion or insertion of an amino acid, which is 90% identical to amino acids 1 to 420 of SEQ ID NO: 4.

4. A detergent composition comprising a surfactant and the polypeptide of claim 1.

* * * * *

```
                         SEQUENCE LISTING

<160> NUMBER OF SEQ ID NOS: 36

<210> SEQ ID NO 1
<211> LENGTH: 1731
<212> TYPE: DNA
<213> ORGANISM: Chaetomium thermophilum
<220> FEATURE:
<221> NAME/KEY: CDS
```

<222> LOCATION: (63)..(1493)

<400> SEQUENCE: 1

| | |
|---|---:|
| cggggggggg ggacagcaca acagagtcaa gacaagcttg gtcgctttgt cagaagttca | 60 |

| | | | | | | | | | | | | | | | | |
|---|---|---|---|---|---|---|---|---|---|---|---|---|---|---|---|---:|
| tc | atg | gct | aag | cag | ctg | ctg | ctc | act | gcc | gct | ctt | gcg | gcc | act | tcg | 107 |
| | Met | Ala | Lys | Gln | Leu | Leu | Leu | Thr | Ala | Ala | Leu | Ala | Ala | Thr | Ser | |
| | 1 | | | 5 | | | | | 10 | | | | | 15 | | |
| ctg | gct | gcc | cct | ctc | ctt | gag | gag | cgc | cag | agc | tgc | tcc | tcc | gtc | tgg | 155 |
| Leu | Ala | Ala | Pro | Leu | Leu | Glu | Glu | Arg | Gln | Ser | Cys | Ser | Ser | Val | Trp | |
| | | | 20 | | | | | 25 | | | | | 30 | | | |
| ggt | caa | tgc | ggt | ggc | atc | aat | tac | aac | ggc | ccg | acc | tgc | tgc | cag | tcc | 203 |
| Gly | Gln | Cys | Gly | Gly | Ile | Asn | Tyr | Asn | Gly | Pro | Thr | Cys | Cys | Gln | Ser | |
| | | 35 | | | | | 40 | | | | | 45 | | | | |
| ggc | agt | gtt | tgc | act | tac | ctg | aat | gac | tgg | tac | agc | cag | tgc | att | ccc | 251 |
| Gly | Ser | Val | Cys | Thr | Tyr | Leu | Asn | Asp | Trp | Tyr | Ser | Gln | Cys | Ile | Pro | |
| | | 50 | | | | | 55 | | | | | 60 | | | | |
| ggt | cag | gct | cag | ccc | ggc | acg | act | agc | acc | acg | gct | cgg | acc | acc | agc | 299 |
| Gly | Gln | Ala | Gln | Pro | Gly | Thr | Thr | Ser | Thr | Thr | Ala | Arg | Thr | Thr | Ser | |
| 65 | | | | | 70 | | | | | 75 | | | | | | |
| acc | agc | acc | acc | agc | act | tcg | tcg | gtc | cgc | ccg | acc | acc | tcg | aat | acc | 347 |
| Thr | Ser | Thr | Thr | Ser | Thr | Ser | Ser | Val | Arg | Pro | Thr | Thr | Ser | Asn | Thr | |
| 80 | | | | | 85 | | | | | 90 | | | | | 95 | |
| cct | gtg | acg | act | gct | ccc | ccg | acg | acc | atc | ccg | ggc | ggc | gcc | tcg | | 395 |
| Pro | Val | Thr | Thr | Ala | Pro | Pro | Thr | Thr | Thr | Ile | Pro | Gly | Gly | Ala | Ser | |
| | | | 100 | | | | | 105 | | | | | 110 | | | |
| agc | acg | gcc | agc | tac | aac | ggc | aac | ccg | ttt | tcg | ggt | gtt | caa | ctt | tgg | 443 |
| Ser | Thr | Ala | Ser | Tyr | Asn | Gly | Asn | Pro | Phe | Ser | Gly | Val | Gln | Leu | Trp | |
| | | | 115 | | | | | 120 | | | | | 125 | | | |
| gcc | aac | acc | tac | tac | tcg | tcc | gag | gtg | cac | act | ttg | gcc | atc | ccc | agc | 491 |
| Ala | Asn | Thr | Tyr | Tyr | Ser | Ser | Glu | Val | His | Thr | Leu | Ala | Ile | Pro | Ser | |
| | | 130 | | | | | 135 | | | | | 140 | | | | |
| ttg | tct | cct | gag | ctg | gct | gcc | aag | gcc | gcc | aag | gtc | gct | gag | gtt | ccc | 539 |
| Leu | Ser | Pro | Glu | Leu | Ala | Ala | Lys | Ala | Ala | Lys | Val | Ala | Glu | Val | Pro | |
| 145 | | | | | 150 | | | | | 155 | | | | | | |
| agc | ttc | cag | tgg | ctc | gac | cgc | aat | gtg | act | gtt | gac | act | ctc | ttc | tcc | 587 |
| Ser | Phe | Gln | Trp | Leu | Asp | Arg | Asn | Val | Thr | Val | Asp | Thr | Leu | Phe | Ser | |
| 160 | | | | | 165 | | | | | 170 | | | | | 175 | |
| ggc | act | ctt | gcc | gaa | atc | cgc | gcc | gcc | aac | cag | cgc | ggt | gcc | aac | ccg | 635 |
| Gly | Thr | Leu | Ala | Glu | Ile | Arg | Ala | Ala | Asn | Gln | Arg | Gly | Ala | Asn | Pro | |
| | | | 180 | | | | | 185 | | | | | 190 | | | |
| cct | tat | gcc | ggc | att | ttc | gtg | gtt | tat | gac | tta | cca | gac | cgt | gat | tgc | 683 |
| Pro | Tyr | Ala | Gly | Ile | Phe | Val | Val | Tyr | Asp | Leu | Pro | Asp | Arg | Asp | Cys | |
| | | | 195 | | | | | 200 | | | | | 205 | | | |
| gcg | gct | gct | gct | tcg | aac | ggc | gag | tgg | tct | atc | gcc | aac | aat | ggt | gcc | 731 |
| Ala | Ala | Ala | Ala | Ser | Asn | Gly | Glu | Trp | Ser | Ile | Ala | Asn | Asn | Gly | Ala | |
| | | 210 | | | | | 215 | | | | | 220 | | | | |
| aac | aac | tac | aag | cgc | tac | atc | gac | cgg | atc | cgt | gag | ctc | ctt | atc | cag | 779 |
| Asn | Asn | Tyr | Lys | Arg | Tyr | Ile | Asp | Arg | Ile | Arg | Glu | Leu | Leu | Ile | Gln | |
| | 225 | | | | | 230 | | | | | 235 | | | | | |
| tac | tcc | gat | atc | cgc | act | att | ctg | gtc | att | gaa | cct | gat | tcc | ctg | gcc | 827 |
| Tyr | Ser | Asp | Ile | Arg | Thr | Ile | Leu | Val | Ile | Glu | Pro | Asp | Ser | Leu | Ala | |
| 240 | | | | | 245 | | | | | 250 | | | | | 255 | |
| aac | atg | gtc | acc | aac | atg | aac | gtc | cag | aag | tgc | tcg | aac | gct | gcc | tcc | 875 |
| Asn | Met | Val | Thr | Asn | Met | Asn | Val | Gln | Lys | Cys | Ser | Asn | Ala | Ala | Ser | |
| | | | 260 | | | | | 265 | | | | | 270 | | | |
| act | tac | aag | gag | ctt | act | gtc | tat | gcc | ctc | aaa | cag | ctc | aat | ctt | cct | 923 |
| Thr | Tyr | Lys | Glu | Leu | Thr | Val | Tyr | Ala | Leu | Lys | Gln | Leu | Asn | Leu | Pro | |
| | | | 275 | | | | | 280 | | | | | 285 | | | |
| cac | gtt | gcc | atg | tac | atg | gat | gct | ggc | cac | gct | ggc | tgg | ctt | ggc | tgg | 971 |

```
                His Val Ala Met Tyr Met Asp Ala Gly His Ala Gly Trp Leu Gly Trp
                        290                 295                 300 ccc gcc aac atc cag cct gct gct gag ctc ttt gct caa atc tac cgc        1019
Pro Ala Asn Ile Gln Pro Ala Ala Glu Leu Phe Ala Gln Ile Tyr Arg
                305                 310                 315 gac gct ggc agg ccc gct gct gtc cgc ggt ctt gcg acc aac gtt gcc        1067
Asp Ala Gly Arg Pro Ala Ala Val Arg Gly Leu Ala Thr Asn Val Ala
320                 325                 330                 335 aac tac aat gct tgg tcg atc gcc agc cct ccg tcc tac acc tct cct        1115
Asn Tyr Asn Ala Trp Ser Ile Ala Ser Pro Pro Ser Tyr Thr Ser Pro
                340                 345                 350 aac ccg aac tac gac gag aag cac tat att gag gcc ttt gct cct ctt        1163
Asn Pro Asn Tyr Asp Glu Lys His Tyr Ile Glu Ala Phe Ala Pro Leu
                355                 360                 365 ctc cgc aac cag ggc ttc gac gca aag ttc atc gtc gac acc ggc cgt        1211
Leu Arg Asn Gln Gly Phe Asp Ala Lys Phe Ile Val Asp Thr Gly Arg
                370                 375                 380 aac ggc aag cag ccc act ggc cag ctt gaa tgg ggt cac tgg tgc aat        1259
Asn Gly Lys Gln Pro Thr Gly Gln Leu Glu Trp Gly His Trp Cys Asn
                385                 390                 395 gtc aag gga act ggc ttc ggt gtg cgc cct act gct aac act ggg cat        1307
Val Lys Gly Thr Gly Phe Gly Val Arg Pro Thr Ala Asn Thr Gly His
400                 405                 410                 415 gaa ctt gtt gat gct ttc gtg tgg gtc aag ccc ggt ggc gag tcc gac        1355
Glu Leu Val Asp Ala Phe Val Trp Val Lys Pro Gly Gly Glu Ser Asp
                420                 425                 430 ggc acc agt gcg gac acc agc gct gct cgt tat gac tat cac tgc ggc        1403
Gly Thr Ser Ala Asp Thr Ser Ala Ala Arg Tyr Asp Tyr His Cys Gly
                435                 440                 445 ctt tcc gac gca ctg act ccg gcg cct gag gct ggc caa tgg ttc cag        1451
Leu Ser Asp Ala Leu Thr Pro Ala Pro Glu Ala Gly Gln Trp Phe Gln
                450                 455                 460 gct tat ttc gaa cag ctg ctc atc aat gcc aac cct ccg ctc                1493
Ala Tyr Phe Glu Gln Leu Leu Ile Asn Ala Asn Pro Pro Leu
                465                 470                 475 tgaacggaag cggagatacc ggaaggcggt gagaagagcg gaattcaagt ctgcttatca      1553
aaatccactc accaagtgga ttaaagcgga tttatacatc tgagaaacaa cctgctttaa      1613
actcttcttg tacatatttc acttcgagac gtgcctcttt ctcaggagca ctgtagatac      1673
caatatatct gtcacatttc ataaaaaaa aaaaaaaaag aaaaaaagta ctagtcga        1731

<210> SEQ ID NO 2
<211> LENGTH: 477
<212> TYPE: PRT
<213> ORGANISM: Chaetomium thermophilum

<400> SEQUENCE: 2

Met Ala Lys Gln Leu Leu Leu Thr Ala Ala Leu Ala Ala Thr Ser Leu
1               5                   10                  15

Ala Ala Pro Leu Leu Glu Glu Arg Gln Ser Cys Ser Ser Val Trp Gly
                20                  25                  30

Gln Cys Gly Gly Ile Asn Tyr Asn Gly Pro Thr Cys Cys Gln Ser Gly
            35                  40                  45

Ser Val Cys Thr Tyr Leu Asn Asp Trp Tyr Ser Gln Cys Ile Pro Gly
        50                  55                  60

Gln Ala Gln Pro Gly Thr Thr Ser Thr Ala Arg Thr Thr Ser Thr
65                  70                  75                  80

Ser Thr Thr Ser Thr Ser Ser Val Arg Pro Thr Thr Ser Asn Thr Pro
```

```
                    85                  90                  95
Val Thr Thr Ala Pro Thr Thr Ile Pro Gly Gly Ala Ser Ser
                100                 105                 110
Thr Ala Ser Tyr Asn Gly Asn Pro Phe Ser Gly Val Gln Leu Trp Ala
                115                 120                 125
Asn Thr Tyr Tyr Ser Ser Glu Val His Thr Leu Ala Ile Pro Ser Leu
            130                 135                 140
Ser Pro Glu Leu Ala Ala Lys Ala Ala Lys Val Ala Glu Val Pro Ser
145                 150                 155                 160
Phe Gln Trp Leu Asp Arg Asn Val Thr Val Asp Thr Leu Phe Ser Gly
                165                 170                 175
Thr Leu Ala Glu Ile Arg Ala Ala Asn Gln Arg Gly Ala Asn Pro Pro
            180                 185                 190
Tyr Ala Gly Ile Phe Val Val Tyr Asp Leu Pro Asp Arg Asp Cys Ala
        195                 200                 205
Ala Ala Ala Ser Asn Gly Glu Trp Ser Ile Ala Asn Asn Gly Ala Asn
    210                 215                 220
Asn Tyr Lys Arg Tyr Ile Asp Arg Ile Arg Glu Leu Leu Ile Gln Tyr
225                 230                 235                 240
Ser Asp Ile Arg Thr Ile Leu Val Ile Glu Pro Asp Ser Leu Ala Asn
                245                 250                 255
Met Val Thr Asn Met Asn Val Gln Lys Cys Ser Asn Ala Ala Ser Thr
            260                 265                 270
Tyr Lys Glu Leu Thr Val Tyr Ala Leu Lys Gln Leu Asn Leu Pro His
        275                 280                 285
Val Ala Met Tyr Met Asp Ala Gly His Ala Gly Trp Leu Gly Trp Pro
    290                 295                 300
Ala Asn Ile Gln Pro Ala Ala Glu Leu Phe Ala Gln Ile Tyr Arg Asp
305                 310                 315                 320
Ala Gly Arg Pro Ala Ala Val Arg Gly Leu Ala Thr Asn Val Ala Asn
                325                 330                 335
Tyr Asn Ala Trp Ser Ile Ala Ser Pro Pro Ser Tyr Thr Ser Pro Asn
            340                 345                 350
Pro Asn Tyr Asp Glu Lys His Tyr Ile Glu Ala Phe Ala Pro Leu Leu
        355                 360                 365
Arg Asn Gln Gly Phe Asp Ala Lys Phe Ile Val Asp Thr Gly Arg Asn
    370                 375                 380
Gly Lys Gln Pro Thr Gly Gln Leu Glu Trp Gly His Trp Cys Asn Val
385                 390                 395                 400
Lys Gly Thr Gly Phe Gly Val Arg Pro Thr Ala Asn Thr Gly His Glu
                405                 410                 415
Leu Val Asp Ala Phe Val Trp Val Lys Pro Gly Gly Glu Ser Asp Gly
            420                 425                 430
Thr Ser Ala Asp Thr Ser Ala Ala Arg Tyr Asp Tyr His Cys Gly Leu
        435                 440                 445
Ser Asp Ala Leu Thr Pro Ala Pro Glu Ala Gly Gln Trp Phe Gln Ala
    450                 455                 460
Tyr Phe Glu Gln Leu Leu Ile Asn Ala Asn Pro Pro Leu
465                 470                 475

<210> SEQ ID NO 3
<211> LENGTH: 1272
<212> TYPE: DNA
<213> ORGANISM: Myceliophthora thermophila
```

```
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t

<400> SEQUENCE: 3
acgtggatcc gaattcaagc ttcatggggt tctcctgcga tccactagta acggctcgcc        60
ngagagctgg aaagccagca gcacctnttg gagaggcagc tctctctctc caccacgccc       120
ccgcccgtct ccagccctcg tgaccagcat tcccggcggt gcgacctcca cggcgagcta       180
ctctggcaac cccttctcgg cgtccggcct cttcgccaac gactactaca ggtccgaggt       240
ccacaatctc gccattccta gcatgactgg tactctggcg gctcaaggct tccgccgtcg       300
cgcgaagtcc ctagcttcca gtggctcgac acggaacgtg cactcatcag acaccctgat       360
ggtccagact ctgtacccag gtccgggctc tcaataaggc acggtgaaca atcctacccn       420
tatgctgccc aactcgtcgt ctacgacctc cccgaccgtg actgtgccgc cgctgcgtcc       480
aacggygagt tttcgattgc aaacggcggc gccgccaact acaggagcta catcgacgct       540
atccgcaagc acatcattga gtactcggac atccggatca tcctggttat cgagcccgac       600
tcgatggcca acatggtgac caacatgaac gtggccaagt gcagcaacgc cgcgtcgacg       660
taccacgagt tgaccgtgta cgcgctcaag cagctgaacc tgcccaacgt cgccatgtat       720
ctcgacgccg ccacgccggg ctggctcggc tggcccgcca acatccagcc cgccgccgag       780
ctgtttgccg gcatctacaa tgatgccggc aagccggctg ccgtccgcgg cctggccact       840
aacgtcgcca actacaacgc ctggagcatc gcttcggccc cgtcgtacac gtcggctaac       900
cctaactacg acgagaagca ctacatcgag gccttcagcc cgctcttgaa ctcggccggc       960
ttccccgcac gcttcattgt cgacactggc cgcaacggca acaacctac cggccaacaa      1020 cagtggggcg actggtgcaa tgtcaagggc accggctttg gcgtgcgccc gacggccaac      1080
acgggccacg agctggtcga tgcctttgtc tgggtcaagc ccggcggcga gtccgacggc      1140
acaagcgaca ccagcgccgc ccgctacgac taccactgcg gcctgtccga tgccctgcag      1200
cctgcccccg aggctggaca gtggttccag gcctacttcg agcagctgct caccaacgcc      1260
aacccgccct tc                                                         1272

<210> SEQ ID NO 4
<211> LENGTH: 420
<212> TYPE: PRT
<213> ORGANISM: Myceliophthora thermophila

<400> SEQUENCE: 4

Thr Trp Ile Arg Ile Gln Ala Ser Trp Gly Ser Pro Ala Ile His Arg
1               5                   10                  15

Leu Ala Glu Leu Glu Ser Gln Gln His Leu Leu Glu Arg Gln Leu Ser
                20                  25                  30

Leu Ser Thr Thr Pro Pro Val Ser Ser Pro Arg Asp Gln His Ser
            35                  40                  45

Arg Arg Cys Asp Leu His Gly Glu Leu Leu Trp Gln Pro Leu Leu Gly
        50                  55                  60
```

```
Arg Pro Ala Leu Arg Gln Arg Leu Leu Gln Val Arg Gly Pro Gln Ser
 65                  70                  75                  80

Arg His Ser His Asp Trp Tyr Ser Gly Gly Ser Arg Leu Pro Pro Ser
                 85                  90                  95

Arg Glu Val Pro Ser Phe Gln Trp Leu Asp Thr Glu Arg Ala Leu Ile
            100                 105                 110

Arg His Pro Asp Gly Pro Asp Ser Val Pro Arg Ser Gly Leu Ser Ile
        115                 120                 125

Arg His Gly Glu Gln Ser Tyr Pro Tyr Ala Ala Gln Leu Val Val Tyr
    130                 135                 140

Asp Leu Pro Asp Arg Asp Cys Ala Ala Ala Ser Asn Gly Glu Phe
145                 150                 155                 160

Ser Ile Ala Asn Gly Gly Ala Ala Asn Tyr Arg Ser Tyr Ile Asp Ala
                165                 170                 175

Ile Arg Lys His Ile Ile Glu Tyr Ser Asp Ile Arg Ile Ile Leu Val
            180                 185                 190

Ile Glu Pro Asp Ser Met Ala Asn Met Val Thr Asn Met Asn Val Ala
        195                 200                 205

Lys Cys Ser Asn Ala Ala Ser Thr Tyr His Glu Leu Thr Val Tyr Ala
210                 215                 220

Leu Lys Gln Leu Asn Leu Pro Asn Val Ala Met Tyr Leu Asp Ala Gly
225                 230                 235                 240

His Ala Gly Trp Leu Gly Trp Pro Ala Asn Ile Gln Pro Ala Ala Glu
                245                 250                 255

Leu Phe Ala Gly Ile Tyr Asn Asp Ala Gly Lys Pro Ala Ala Val Arg
            260                 265                 270

Gly Leu Ala Thr Asn Val Ala Asn Tyr Asn Ala Trp Ser Ile Ala Ser
        275                 280                 285

Ala Pro Ser Tyr Thr Ser Ala Asn Pro Asn Tyr Asp Glu Lys His Tyr
    290                 295                 300

Ile Glu Ala Phe Ser Pro Leu Leu Asn Ser Ala Gly Phe Pro Ala Arg
305                 310                 315                 320

Phe Ile Val Asp Thr Gly Arg Asn Gly Lys Gln Pro Thr Gly Gln Gln
                325                 330                 335

Gln Trp Gly Asp Trp Cys Asn Val Lys Gly Thr Gly Phe Gly Val Arg
            340                 345                 350

Pro Thr Ala Asn Thr Gly His Glu Leu Val Asp Ala Phe Val Trp Val
        355                 360                 365

Lys Pro Gly Gly Glu Ser Asp Gly Thr Ser Asp Thr Ser Ala Ala Arg
    370                 375                 380

Tyr Asp Tyr His Cys Gly Leu Ser Asp Ala Leu Gln Pro Ala Pro Glu
385                 390                 395                 400

Ala Gly Gln Trp Phe Gln Ala Tyr Phe Glu Gln Leu Leu Thr Asn Ala
                405                 410                 415

Asn Pro Pro Phe
            420

<210> SEQ ID NO 5
<211> LENGTH: 419
<212> TYPE: DNA
<213> ORGANISM: Acremonium sp.
<220> FEATURE:
<221> NAME/KEY: CDS
<222> LOCATION: (1)..(417)

<400> SEQUENCE: 5
```

```
tac gca agt gtc tac tcg gac gcc gga tca ccg gct gca ctc cgc ggt        48
Tyr Ala Ser Val Tyr Ser Asp Ala Gly Ser Pro Ala Ala Leu Arg Gly
1               5                   10                  15 ctc gct acc aac gtc gcc aat tac aac gcc tgg aca atc gat acc tgc        96
Leu Ala Thr Asn Val Ala Asn Tyr Asn Ala Trp Thr Ile Asp Thr Cys
                20                  25                  30 cct tca tac aca cag ggt aac tcc att tgc gac gag aag gac tac atc       144
Pro Ser Tyr Thr Gln Gly Asn Ser Ile Cys Asp Glu Lys Asp Tyr Ile
            35                  40                  45 aat gcg ctt gct ccc ctg ctt cgc agc tca ggg ctt acg gac gct cat       192
Asn Ala Leu Ala Pro Leu Leu Arg Ser Ser Gly Leu Thr Asp Ala His
    50                  55                  60 ttc atc act gat acc ggc cgc aac ggc aag caa cca aca ggc caa caa       240
Phe Ile Thr Asp Thr Gly Arg Asn Gly Lys Gln Pro Thr Gly Gln Gln
65                  70                  75                  80 gcc tgg ggc gac tgg tgc aat gtc atc ggc acg ggc ttt ggc gtg cgc       288
Ala Trp Gly Asp Trp Cys Asn Val Ile Gly Thr Gly Phe Gly Val Arg
                85                  90                  95 ccg tcc acg aac aca ggt gat tct tta ctt gac gcc ttc gtc tgg gtt       336
Pro Ser Thr Asn Thr Gly Asp Ser Leu Leu Asp Ala Phe Val Trp Val
            100                 105                 110 aaa ccc ggt ggc gag agt gac ggg act tct gat act tgt gcg gcg cgg       384
Lys Pro Gly Gly Glu Ser Asp Gly Thr Ser Asp Thr Cys Ala Ala Arg
    115                 120                 125 tat gat gcg cat tgc ggg tat agc gat gcg ctg ca                        419
Tyr Asp Ala His Cys Gly Tyr Ser Asp Ala Leu
130                 135

<210> SEQ ID NO 6
<211> LENGTH: 139
<212> TYPE: PRT
<213> ORGANISM: Acremonium sp.

<400> SEQUENCE: 6

Tyr Ala Ser Val Tyr Ser Asp Ala Gly Ser Pro Ala Ala Leu Arg Gly
1               5                   10                  15

Leu Ala Thr Asn Val Ala Asn Tyr Asn Ala Trp Thr Ile Asp Thr Cys
                20                  25                  30

Pro Ser Tyr Thr Gln Gly Asn Ser Ile Cys Asp Glu Lys Asp Tyr Ile
            35                  40                  45

Asn Ala Leu Ala Pro Leu Leu Arg Ser Ser Gly Leu Thr Asp Ala His
    50                  55                  60

Phe Ile Thr Asp Thr Gly Arg Asn Gly Lys Gln Pro Thr Gly Gln Gln
65                  70                  75                  80

Ala Trp Gly Asp Trp Cys Asn Val Ile Gly Thr Gly Phe Gly Val Arg
                85                  90                  95

Pro Ser Thr Asn Thr Gly Asp Ser Leu Leu Asp Ala Phe Val Trp Val
            100                 105                 110

Lys Pro Gly Gly Glu Ser Asp Gly Thr Ser Asp Thr Cys Ala Ala Arg
    115                 120                 125

Tyr Asp Ala His Cys Gly Tyr Ser Asp Ala Leu
130                 135

<210> SEQ ID NO 7
<211> LENGTH: 306
<212> TYPE: DNA
<213> ORGANISM: Melanocarpus sp.
<220> FEATURE:
<221> NAME/KEY: CDS
```

```
<222> LOCATION: (1)..(306)

<400> SEQUENCE: 7 gat gcc ggc aag ccg cac tcg gtc cgc ggt ctc gcc acc aac gtc gcc      48
Asp Ala Gly Lys Pro His Ser Val Arg Gly Leu Ala Thr Asn Val Ala
1               5                   10                  15 aac tac aat gcc tgg agc gtc gcc tcg gcc ccg cct tac acc agc ccc      96
Asn Tyr Asn Ala Trp Ser Val Ala Ser Ala Pro Pro Tyr Thr Ser Pro
            20                  25                  30 aac ccc aac tac gat gag aag cac tac att gag gcc ttc agc cct ctc      144
Asn Pro Asn Tyr Asp Glu Lys His Tyr Ile Glu Ala Phe Ser Pro Leu
        35                  40                  45 ctt gag gcc cgc ggc ttc cct gcc cgc ttc atc gtc gac cag ggc cgc      192
Leu Glu Ala Arg Gly Phe Pro Ala Arg Phe Ile Val Asp Gln Gly Arg
    50                  55                  60 agc ggc aag cag ccc acc ggc cag aag gag tgg ggc cac tgg tgc aac      240
Ser Gly Lys Gln Pro Thr Gly Gln Lys Glu Trp Gly His Trp Cys Asn
65                  70                  75                  80 gct atc ggc acc ggc ttc ggc att cgc ccg acc gcc aac acc ggc cac      288
Ala Ile Gly Thr Gly Phe Gly Ile Arg Pro Thr Ala Asn Thr Gly His
                85                  90                  95 aac ctg gtt gat gcc ttc                                              306
Asn Leu Val Asp Ala Phe
            100

<210> SEQ ID NO 8
<211> LENGTH: 102
<212> TYPE: PRT
<213> ORGANISM: Melanocarpus sp.

<400> SEQUENCE: 8

Asp Ala Gly Lys Pro His Ser Val Arg Gly Leu Ala Thr Asn Val Ala
1               5                   10                  15

Asn Tyr Asn Ala Trp Ser Val Ala Ser Ala Pro Pro Tyr Thr Ser Pro
            20                  25                  30

Asn Pro Asn Tyr Asp Glu Lys His Tyr Ile Glu Ala Phe Ser Pro Leu
        35                  40                  45

Leu Glu Ala Arg Gly Phe Pro Ala Arg Phe Ile Val Asp Gln Gly Arg
    50                  55                  60

Ser Gly Lys Gln Pro Thr Gly Gln Lys Glu Trp Gly His Trp Cys Asn
65                  70                  75                  80

Ala Ile Gly Thr Gly Phe Gly Ile Arg Pro Thr Ala Asn Thr Gly His
                85                  90                  95

Asn Leu Val Asp Ala Phe
            100

<210> SEQ ID NO 9
<211> LENGTH: 432
<212> TYPE: DNA
<213> ORGANISM: Thielavia microspora
<220> FEATURE:
<221> NAME/KEY: CDS
<222> LOCATION: (1)..(432)

<400> SEQUENCE: 9 gcc aac atc cag ccc gct gcc acc ctg ttc gcc ggc atc tac agc gac      48
Ala Asn Ile Gln Pro Ala Ala Thr Leu Phe Ala Gly Ile Tyr Ser Asp
1               5                   10                  15 gct ggc aag ccc gcc tcg gtc cgc ggt ttg gcc acc aac gtg gcc aac      96
Ala Gly Lys Pro Ala Ser Val Arg Gly Leu Ala Thr Asn Val Ala Asn
            20                  25                  30
```

```
tac aac gcc tgg agc ctg tcg tcg gcg ccg tcg tac acg agc ccc aac    144
Tyr Asn Ala Trp Ser Leu Ser Ser Ala Pro Ser Tyr Thr Ser Pro Asn
         35                  40                  45 gcc aac tac gac gag aag cac tac gtc gag gcc ttt gcc ccg ctc ctc    192
Ala Asn Tyr Asp Glu Lys His Tyr Val Glu Ala Phe Ala Pro Leu Leu
 50                  55                  60 cag gcg gcc ggc ttc ccc gcc aag ttc atc acc gac acg ggc cgc aac    240
Gln Ala Ala Gly Phe Pro Ala Lys Phe Ile Thr Asp Thr Gly Arg Asn
 65                  70                  75                  80 ggc aag cag ccc acg ggc cag agc gcg tgg ggc gac tgg tgc aac gtc    288
Gly Lys Gln Pro Thr Gly Gln Ser Ala Trp Gly Asp Trp Cys Asn Val
             85                  90                  95 aag ggc acc ggc ttc ggt gtc cgc ccg acc tcg gag acg ggc cac gac    336
Lys Gly Thr Gly Phe Gly Val Arg Pro Thr Ser Glu Thr Gly His Asp
            100                 105                 110 ctc ctc gac gcc ttc gtc tgg gtc aag ccc ggt ggc gag tcg gac ggc    384
Leu Leu Asp Ala Phe Val Trp Val Lys Pro Gly Gly Glu Ser Asp Gly
            115                 120                 125 acc agc gac acc agc gcc gcc cgc tac gac tac cac tgc ggt ctg tcg    432
Thr Ser Asp Thr Ser Ala Ala Arg Tyr Asp Tyr His Cys Gly Leu Ser
        130                 135                 140

<210> SEQ ID NO 10
<211> LENGTH: 144
<212> TYPE: PRT
<213> ORGANISM: Thielavia microspora

<400> SEQUENCE: 10

Ala Asn Ile Gln Pro Ala Ala Thr Leu Phe Ala Gly Ile Tyr Ser Asp
 1               5                  10                  15

Ala Gly Lys Pro Ala Ser Val Arg Gly Leu Ala Thr Asn Val Ala Asn
             20                  25                  30

Tyr Asn Ala Trp Ser Leu Ser Ser Ala Pro Ser Tyr Thr Ser Pro Asn
         35                  40                  45

Ala Asn Tyr Asp Glu Lys His Tyr Val Glu Ala Phe Ala Pro Leu Leu
 50                  55                  60

Gln Ala Ala Gly Phe Pro Ala Lys Phe Ile Thr Asp Thr Gly Arg Asn
 65                  70                  75                  80

Gly Lys Gln Pro Thr Gly Gln Ser Ala Trp Gly Asp Trp Cys Asn Val
             85                  90                  95

Lys Gly Thr Gly Phe Gly Val Arg Pro Thr Ser Glu Thr Gly His Asp
            100                 105                 110

Leu Leu Asp Ala Phe Val Trp Val Lys Pro Gly Gly Glu Ser Asp Gly
            115                 120                 125

Thr Ser Asp Thr Ser Ala Ala Arg Tyr Asp Tyr His Cys Gly Leu Ser
        130                 135                 140

<210> SEQ ID NO 11
<211> LENGTH: 297
<212> TYPE: DNA
<213> ORGANISM: Aspergillus
<220> FEATURE:
<221> NAME/KEY: CDS
<222> LOCATION: (1)..(297)

<400> SEQUENCE: 11 gga ttg ttt ggg tgg cct gcc aac ctt act cct tcc gct cgt ctc ttc     48
Gly Leu Phe Gly Trp Pro Ala Asn Leu Thr Pro Ser Ala Arg Leu Phe
 1               5                  10                  15
```

-continued

```
gcc caa atc tac aag gat gcc ggc agg tct gcc ttc atc cgt ggt ctt     96
Ala Gln Ile Tyr Lys Asp Ala Gly Arg Ser Ala Phe Ile Arg Gly Leu
         20                  25                  30 gcc acc aac gtc tcc aac tac aac gcc ctc agt gca acc acc cgt gat    144
Ala Thr Asn Val Ser Asn Tyr Asn Ala Leu Ser Ala Thr Thr Arg Asp
     35                  40                  45 ccc gtc acc cag ggc aat gac aac tac gat gag ctc cgc ttc atc aac    192
Pro Val Thr Gln Gly Asn Asp Asn Tyr Asp Glu Leu Arg Phe Ile Asn
 50                  55                  60 gct ctt gct cct ctc ctc cga aat gaa ggc tgg gac gcc aag ttc atc    240
Ala Leu Ala Pro Leu Leu Arg Asn Glu Gly Trp Asp Ala Lys Phe Ile
 65                  70                  75                  80 gtc gac cag ggt cgt tct ggt gtc cag aac atc cga cag gag tgg ggc    288
Val Asp Gln Gly Arg Ser Gly Val Gln Asn Ile Arg Gln Glu Trp Gly
                 85                  90                  95 gac tgg tgc                                                        297
Asp Trp Cys
```

<210> SEQ ID NO 12
<211> LENGTH: 99
<212> TYPE: PRT
<213> ORGANISM: Aspergillus

<400> SEQUENCE: 12

```
Gly Leu Phe Gly Trp Pro Ala Asn Leu Thr Pro Ser Ala Arg Leu Phe
 1               5                  10                  15

Ala Gln Ile Tyr Lys Asp Ala Gly Arg Ser Ala Phe Ile Arg Gly Leu
             20                  25                  30

Ala Thr Asn Val Ser Asn Tyr Asn Ala Leu Ser Ala Thr Thr Arg Asp
         35                  40                  45

Pro Val Thr Gln Gly Asn Asp Asn Tyr Asp Glu Leu Arg Phe Ile Asn
     50                  55                  60

Ala Leu Ala Pro Leu Leu Arg Asn Glu Gly Trp Asp Ala Lys Phe Ile
 65                  70                  75                  80

Val Asp Gln Gly Arg Ser Gly Val Gln Asn Ile Arg Gln Glu Trp Gly
                 85                  90                  95

Asp Trp Cys
```

<210> SEQ ID NO 13
<211> LENGTH: 420
<212> TYPE: DNA
<213> ORGANISM: Thielavia australiensis
<220> FEATURE:
<221> NAME/KEY: CDS
<222> LOCATION: (1)..(420)

<400> SEQUENCE: 13

```
tgg ctg ggg tgg ccc gcc aac atc cag ccc gct gct acc ctg ttc gcc     48
Trp Leu Gly Trp Pro Ala Asn Ile Gln Pro Ala Ala Thr Leu Phe Ala
 1               5                  10                  15 ggc atc tac aac gac gct ggc aag ccc gcc tcg gtc cgt ggt ctg gcc     96
Gly Ile Tyr Asn Asp Ala Gly Lys Pro Ala Ser Val Arg Gly Leu Ala
             20                  25                  30 acc aac gtt gcc aac tac aac gcc tgg agc ctg tcc tcg gcc ccg tcg    144
Thr Asn Val Ala Asn Tyr Asn Ala Trp Ser Leu Ser Ser Ala Pro Ser
         35                  40                  45 tac acg acc ccc aac gcc aac tac gac gag aag cac tac gtc gag gcc    192
Tyr Thr Thr Pro Asn Ala Asn Tyr Asp Glu Lys His Tyr Val Glu Ala
     50                  55                  60 ttt gcc ccg ctt ctc tcg gcc gct ggc ttc ccc gcc aag ttc atc acc    240
```

```
                                                                             -continued Phe Ala Pro Leu Leu Ser Ala Ala Gly Phe Pro Ala Lys Phe Ile Thr
 65                  70                  75                  80 gac act ggc cgc aac ggc aag cag ccc acc ggc cag agc cag tgg ggc          288
Asp Thr Gly Arg Asn Gly Lys Gln Pro Thr Gly Gln Ser Gln Trp Gly
                 85                  90                  95 gat tgg tgc aac gtc aag ggc acc ggc ttc ggt gtc cgc ccg acc tcc          336
Asp Trp Cys Asn Val Lys Gly Thr Gly Phe Gly Val Arg Pro Thr Ser
            100                 105                 110 gag acg ggc cac gag ctc ctg gat gcc ttt gtc tgg gcc aag ccc ggt          384
Glu Thr Gly His Glu Leu Leu Asp Ala Phe Val Trp Ala Lys Pro Gly
        115                 120                 125 ggc gag tcc gac ggt acc agc gac acc agc gct gcc                          420
Gly Glu Ser Asp Gly Thr Ser Asp Thr Ser Ala Ala
    130                 135                 140

<210> SEQ ID NO 14
<211> LENGTH: 140
<212> TYPE: PRT
<213> ORGANISM: Thielavia australiensis

<400> SEQUENCE: 14

Trp Leu Gly Trp Pro Ala Asn Ile Gln Pro Ala Ala Thr Leu Phe Ala
 1               5                  10                  15

Gly Ile Tyr Asn Asp Ala Gly Lys Pro Ala Ser Val Arg Gly Leu Ala
             20                  25                  30

Thr Asn Val Ala Asn Tyr Asn Ala Trp Ser Leu Ser Ser Ala Pro Ser
         35                  40                  45

Tyr Thr Thr Pro Asn Ala Asn Tyr Asp Glu Lys His Tyr Val Glu Ala
     50                  55                  60

Phe Ala Pro Leu Leu Ser Ala Ala Gly Phe Pro Ala Lys Phe Ile Thr
 65                  70                  75                  80

Asp Thr Gly Arg Asn Gly Lys Gln Pro Thr Gly Gln Ser Gln Trp Gly
                 85                  90                  95

Asp Trp Cys Asn Val Lys Gly Thr Gly Phe Gly Val Arg Pro Thr Ser
            100                 105                 110

Glu Thr Gly His Glu Leu Leu Asp Ala Phe Val Trp Ala Lys Pro Gly
        115                 120                 125

Gly Glu Ser Asp Gly Thr Ser Asp Thr Ser Ala Ala
    130                 135                 140

<210> SEQ ID NO 15
<211> LENGTH: 1221
<212> TYPE: DNA
<213> ORGANISM: Aspergillus tubingensis
<220> FEATURE:
<221> NAME/KEY: CDS
<222> LOCATION: (1)..(1221)
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t

<400> SEQUENCE: 15 atg aat atg cac tcc atc aac atg cga gcc atc tgg ccc ctc gtc tct           48
Met Asn Met His Ser Ile Asn Met Arg Ala Ile Trp Pro Leu Val Ser
```

-continued

| | |
|---|---|
| ctc ttc tct gcc gtt aag gcc ctc ccc gcc gca agc gcg act gct tca<br>Leu Phe Ser Ala Val Lys Ala Leu Pro Ala Ala Ser Ala Thr Ala Ser<br>20                25                30 | 96 |
| gcg tct gtt gcg gcc tcg agc tct ccg gcg ccg act gcc tct gct acc<br>Ala Ser Val Ala Ala Ser Ser Ser Pro Ala Pro Thr Ala Ser Ala Thr<br>    35                40                45 | 144 |
| ggc aat ccc ttt gag gga tac cag ctc tat gtg aac ccc tac tat aag<br>Gly Asn Pro Phe Glu Gly Tyr Gln Leu Tyr Val Asn Pro Tyr Tyr Lys<br>50                55                60 | 192 |
| tcg caa gtg gag agt tcg gcc att cca tca ttg tct gct agt tcg ctg<br>Ser Gln Val Glu Ser Ser Ala Ile Pro Ser Leu Ser Ala Ser Ser Leu<br>65                70                75                80 | 240 |
| gtc gcg cag gcg agt gct gca gcc gat gtg cct tca ttt tac tgg cta<br>Val Ala Gln Ala Ser Ala Ala Asp Val Pro Ser Phe Tyr Trp Leu<br>            85                90                95 | 288 |
| gac acg gcc gac aag gtg cct acc atg ggt gaa tat ctg gat gac atc<br>Asp Thr Ala Asp Lys Val Pro Thr Met Gly Glu Tyr Leu Asp Asp Ile<br>            100               105               110 | 336 |
| cag acg caa aac gcc gct gga gcg aat cct ccc att gct ggt atc ttc<br>Gln Thr Gln Asn Ala Ala Gly Ala Asn Pro Pro Ile Ala Gly Ile Phe<br>        115               120               125 | 384 |
| gtc gtc tat gac ctg ccg gat cgg gat tgc gct gcc ttg gct agt aat<br>Val Val Tyr Asp Leu Pro Asp Arg Asp Cys Ala Ala Leu Ala Ser Asn<br>130               135               140 | 432 |
| ggg gaa tac gcg atc agt gat gga ggc gtg gag aag tat aag gcg tac<br>Gly Glu Tyr Ala Ile Ser Asp Gly Gly Val Glu Lys Tyr Lys Ala Tyr<br>145               150               155               160 | 480 |
| att gat tct att cgc gag cag gtc gag acg tac tcg gat gtt cag act<br>Ile Asp Ser Ile Arg Glu Gln Val Glu Thr Tyr Ser Asp Val Gln Thr<br>                165               170               175 | 528 |
| att ttg att atc gaa ccg gat agc tta gct aac ctg gtg acg aat ctc<br>Ile Leu Ile Ile Glu Pro Asp Ser Leu Ala Asn Leu Val Thr Asn Leu<br>            180               185               190 | 576 |
| gat gtg gct aaa tgc gcc aat gct caa tct gct tac ctg gaa tgc acc<br>Asp Val Ala Lys Cys Ala Asn Ala Gln Ser Ala Tyr Leu Glu Cys Thr<br>        195               200               205 | 624 |
| aat tat gca ctt gag cag ttg aat ctr ccg aac gtg gct atg tat ctt<br>Asn Tyr Ala Leu Glu Gln Leu Asn Xaa Pro Asn Val Ala Met Tyr Leu<br>210               215               220 | 672 |
| gat gct ggc cat gct gga tgg ctg gga tgg cct gcc aac atc ggt ccc<br>Asp Ala Gly His Ala Gly Trp Leu Gly Trp Pro Ala Asn Ile Gly Pro<br>225               230               235               240 | 720 |
| gcg gcg gaa ctc tac gca tcg gtg tat aag aat gcg tcg tct cca gca<br>Ala Ala Glu Leu Tyr Ala Ser Val Tyr Lys Asn Ala Ser Ser Pro Ala<br>                245               250               255 | 768 |
| gct gtt cgt gga ctc gct aca rac gta gct aac ttc aat gcc tgg agc<br>Ala Val Arg Gly Leu Ala Thr Xaa Val Ala Asn Phe Asn Ala Trp Ser<br>            260               265               270 | 816 |
| atc gac act tgc ccc tcc tat acw tcg ggt aac gat gtc tgt gat gaa<br>Ile Asp Thr Cys Pro Ser Tyr Xaa Ser Gly Asn Asp Val Cys Asp Glu<br>        275               280               285 | 864 |
| aaa agc tac atc aat gcc ttt gca ccg gag ctc tct agn gct gga ttt<br>Lys Ser Tyr Ile Asn Ala Phe Ala Pro Glu Leu Ser Xaa Ala Gly Phe<br>290               295               300 | 912 |
| gat gcc cac ttt att acc gat acg ggt cgc aat gga aag cag cct act<br>Asp Ala His Phe Ile Thr Asp Thr Gly Arg Asn Gly Lys Gln Pro Thr<br>305               310               315               320 | 960 |
| gga caa agc gcg tgg ggt gac tgg ggc aat gtc aag gat act ggc ttc | 1008 |

```
Gly Gln Ser Ala Trp Gly Asp Trp Gly Asn Val Lys Asp Thr Gly Phe
                325                 330                 335 ggn gct can ccg aca acc gat act gga aac gag ctg gct gat gcc ttt      1056
Gly Ala Xaa Pro Thr Thr Asp Thr Gly Asn Glu Leu Ala Asp Ala Phe
                340                 345                 350 gtc tgg gyc aac cct ggc gga aag agt gat ggg acg tcg gac act agc      1104
Val Trp Xaa Asn Pro Gly Gly Lys Ser Asp Gly Thr Ser Asp Thr Ser
                355                 360                 365 tct tct cgc tac gat gcg cat tgc gga tat agt gat gct ttg cag cct      1152
Ser Ser Arg Tyr Asp Ala His Cys Gly Tyr Ser Asp Ala Leu Gln Pro
        370                 375                 380 gcc ccg gag gct ggt act tgg ttc cag gca tac ttt gag cag ctt ttg      1200
Ala Pro Glu Ala Gly Thr Trp Phe Gln Ala Tyr Phe Glu Gln Leu Leu
385                 390                 395                 400 acc aat gcc aac cct tcc ctg                                          1221
Thr Asn Ala Asn Pro Ser Leu
                405
```

<210> SEQ ID NO 16
<211> LENGTH: 407
<212> TYPE: PRT
<213> ORGANISM: Aspergillus tubingensis
<220> FEATURE:
<221> NAME/KEY: misc_feature
<222> LOCATION: (217)..(217)
<223> OTHER INFORMATION: The 'Xaa' at location 217 stands for Leu.
<220> FEATURE:
<221> NAME/KEY: misc_feature
<222> LOCATION: (264)..(264)
<223> OTHER INFORMATION: The 'Xaa' at location 264 stands for Asp, or
      Asn.
<220> FEATURE:
<221> NAME/KEY: misc_feature
<222> LOCATION: (280)..(280)
<223> OTHER INFORMATION: The 'Xaa' at location 280 stands for Thr.
<220> FEATURE:
<221> NAME/KEY: misc_feature
<222> LOCATION: (301)..(301)
<223> OTHER INFORMATION: The 'Xaa' at location 301 stands for Arg, or
      Ser.
<220> FEATURE:
<221> NAME/KEY: misc_feature
<222> LOCATION: (339)..(339)
<223> OTHER INFORMATION: The 'Xaa' at location 339 stands for Gln, or
      His.
<220> FEATURE:
<221> NAME/KEY: misc_feature
<222> LOCATION: (355)..(355)
<223> OTHER INFORMATION: The 'Xaa' at location 355 stands for Ala, or
      Val.

<400> SEQUENCE: 16

```
Met Asn Met His Ser Ile Asn Met Arg Ala Ile Trp Pro Leu Val Ser
1               5                   10                  15

Leu Phe Ser Ala Val Lys Ala Leu Pro Ala Ala Ser Ala Thr Ala Ser
                20                  25                  30

Ala Ser Val Ala Ala Ser Ser Pro Ala Pro Thr Ala Ser Ala Thr
                35                  40                  45

Gly Asn Pro Phe Glu Gly Tyr Gln Leu Tyr Val Asn Pro Tyr Tyr Lys
        50                  55                  60

Ser Gln Val Glu Ser Ser Ala Ile Pro Ser Leu Ser Ala Ser Ser Leu
65                  70                  75                  80

Val Ala Gln Ala Ser Ala Ala Asp Val Pro Ser Phe Tyr Trp Leu
                85                  90                  95

Asp Thr Ala Asp Lys Val Pro Thr Met Gly Glu Tyr Leu Asp Asp Ile
                100                 105                 110
```

```
Gln Thr Gln Asn Ala Ala Gly Ala Asn Pro Pro Ile Ala Gly Ile Phe
            115                 120                 125

Val Val Tyr Asp Leu Pro Asp Arg Asp Cys Ala Ala Leu Ala Ser Asn
        130                 135                 140

Gly Glu Tyr Ala Ile Ser Asp Gly Gly Val Glu Lys Tyr Lys Ala Tyr
145                 150                 155                 160

Ile Asp Ser Ile Arg Glu Gln Val Glu Thr Tyr Ser Asp Val Gln Thr
                165                 170                 175

Ile Leu Ile Ile Glu Pro Asp Ser Leu Ala Asn Leu Val Thr Asn Leu
            180                 185                 190

Asp Val Ala Lys Cys Ala Asn Ala Gln Ser Ala Tyr Leu Glu Cys Thr
        195                 200                 205

Asn Tyr Ala Leu Glu Gln Leu Asn Xaa Pro Asn Val Ala Met Tyr Leu
210                 215                 220

Asp Ala Gly His Ala Gly Trp Leu Gly Trp Pro Ala Asn Ile Gly Pro
225                 230                 235                 240

Ala Ala Glu Leu Tyr Ala Ser Val Tyr Lys Asn Ala Ser Ser Pro Ala
                245                 250                 255

Ala Val Arg Gly Leu Ala Thr Xaa Val Ala Asn Phe Asn Ala Trp Ser
            260                 265                 270

Ile Asp Thr Cys Pro Ser Tyr Xaa Ser Gly Asn Asp Val Cys Asp Glu
        275                 280                 285

Lys Ser Tyr Ile Asn Ala Phe Ala Pro Glu Leu Ser Xaa Ala Gly Phe
290                 295                 300

Asp Ala His Phe Ile Thr Asp Thr Gly Arg Asn Gly Lys Gln Pro Thr
305                 310                 315                 320

Gly Gln Ser Ala Trp Gly Asp Trp Gly Asn Val Lys Asp Thr Gly Phe
                325                 330                 335

Gly Ala Xaa Pro Thr Thr Asp Thr Gly Asn Glu Leu Ala Asp Ala Phe
            340                 345                 350

Val Trp Xaa Asn Pro Gly Gly Lys Ser Asp Gly Thr Ser Asp Thr Ser
        355                 360                 365

Ser Ser Arg Tyr Asp Ala His Cys Gly Tyr Ser Asp Ala Leu Gln Pro
370                 375                 380

Ala Pro Glu Ala Gly Thr Trp Phe Gln Ala Tyr Phe Glu Gln Leu Leu
385                 390                 395                 400

Thr Asn Ala Asn Pro Ser Leu
                405

<210> SEQ ID NO 17
<211> LENGTH: 429
<212> TYPE: DNA
<213> ORGANISM: Gloeophyllum trabeum
<220> FEATURE:
<221> NAME/KEY: CDS
<222> LOCATION: (1)..(429)

<400> SEQUENCE: 17 gca tcg tct cca gca gct gtt cgt gga ctc gct aca aac gta gct aac    48
Ala Ser Ser Pro Ala Ala Val Arg Gly Leu Ala Thr Asn Val Ala Asn
1               5                   10                  15 ttc aat gcc tgg agc atc gac act tgc ccc tcc tat aca tcg ggt aac    96
Phe Asn Ala Trp Ser Ile Asp Thr Cys Pro Ser Tyr Thr Ser Gly Asn
            20                  25                  30 gat gtc tgt gat gag aag agc tac atc aat gcc ttt gca ccg gag ctc    144
Asp Val Cys Asp Glu Lys Ser Tyr Ile Asn Ala Phe Ala Pro Glu Leu
```

```
                   35                  40                  45
tct agt gct gga ttt gat gcc cac ttt att acc gat acg ggt cgc aat       192
Ser Ser Ala Gly Phe Asp Ala His Phe Ile Thr Asp Thr Gly Arg Asn
 50                  55                  60 gga aag cag cct act gga cag agc gcg tgg ggt gac tgg tgc aat gtc       240
Gly Lys Gln Pro Thr Gly Gln Ser Ala Trp Gly Asp Trp Cys Asn Val
 65                  70                  75                  80 aag gat act ggc ttc ggt gct cag ccg acg acc gat act gga gac gag       288
Lys Asp Thr Gly Phe Gly Ala Gln Pro Thr Thr Asp Thr Gly Asp Glu
                 85                  90                  95 ctg gct gat gcc ttt gtc tgg gtc aag cct ggc gga gag agt gat ggg       336
Leu Ala Asp Ala Phe Val Trp Val Lys Pro Gly Gly Glu Ser Asp Gly
            100                 105                 110 acg tcg gac act agc tct tct cgc tac gat gcg cat tgc gga tat agt       384
Thr Ser Asp Thr Ser Ser Ser Arg Tyr Asp Ala His Cys Gly Tyr Ser
        115                 120                 125 gat gct ttg cag cct gcc ccg gag gct ggt act tgg ttc caa ggc           429
Asp Ala Leu Gln Pro Ala Pro Glu Ala Gly Thr Trp Phe Gln Gly
    130                 135                 140

<210> SEQ ID NO 18
<211> LENGTH: 143
<212> TYPE: PRT
<213> ORGANISM: Gloeophyllum trabeum

<400> SEQUENCE: 18

Ala Ser Ser Pro Ala Ala Val Arg Gly Leu Ala Thr Asn Val Ala Asn
 1               5                   10                  15

Phe Asn Ala Trp Ser Ile Asp Thr Cys Pro Ser Tyr Thr Ser Gly Asn
                20                  25                  30

Asp Val Cys Asp Glu Lys Ser Tyr Ile Asn Ala Phe Ala Pro Glu Leu
            35                  40                  45

Ser Ser Ala Gly Phe Asp Ala His Phe Ile Thr Asp Thr Gly Arg Asn
 50                  55                  60

Gly Lys Gln Pro Thr Gly Gln Ser Ala Trp Gly Asp Trp Cys Asn Val
 65                  70                  75                  80

Lys Asp Thr Gly Phe Gly Ala Gln Pro Thr Thr Asp Thr Gly Asp Glu
                85                  90                  95

Leu Ala Asp Ala Phe Val Trp Val Lys Pro Gly Gly Glu Ser Asp Gly
            100                 105                 110

Thr Ser Asp Thr Ser Ser Ser Arg Tyr Asp Ala His Cys Gly Tyr Ser
        115                 120                 125

Asp Ala Leu Gln Pro Ala Pro Glu Ala Gly Thr Trp Phe Gln Gly
    130                 135                 140

<210> SEQ ID NO 19
<211> LENGTH: 213
<212> TYPE: DNA
<213> ORGANISM: Meripilus giganteus ND001631
<220> FEATURE:
<221> NAME/KEY: misc_feature
<222> LOCATION: (1)..(213)
<223> OTHER INFORMATION: y is c or t

<400> SEQUENCE: 19
aaactcggag tacgtctgga acaagtgccg gcctcnggcr gctgggtacc gtcttcgtcc      60
gacagacagc asgtgctgtc gtaccggtrg cgacgagctg ttcgaggtay cgtcggactc     120
ryctccgggm ttcacccaga tkatcacgtc tatgasyggg ttgcccgtgt tcgtcctcat     180
```

```
ggcgcgtgcc gaagccgttg cccttgatgt tgc                                      213
```

```
<210> SEQ ID NO 20
<211> LENGTH: 71
<212> TYPE: PRT
<213> ORGANISM: Meripilus giganteus
<220> FEATURE:
<221> NAME/KEY: MISC_FEATURE
<222> LOCATION: (1)..(71)
<223> OTHER INFORMATION: x is any amino acid

<400> SEQUENCE: 20

Ala Thr Ser Arg Ala Thr Ala Ser Ala Arg Ala Met Arg Thr Asn Thr
1               5                   10                  15

Gly Asn Pro Xaa Ile Asp Val Ile Ile Trp Val Xaa Pro Gly Xaa Glu
            20                  25                  30

Ser Asp Xaa Thr Ser Asn Ser Ser Xaa Pro Val Arg Gln His Xaa
        35                  40                  45

Leu Ser Val Gly Arg Arg Arg Tyr Pro Ala Ala Xaa Gly Arg His Leu
    50                  55                  60

Phe Gln Thr Tyr Ser Glu Phe
65                  70

<210> SEQ ID NO 21
<211> LENGTH: 782
<212> TYPE: DNA
<213> ORGANISM: Trichophaea saccata
<220> FEATURE:
<221> NAME/KEY: CDS
<222> LOCATION: (43)..(702)

<400> SEQUENCE: 21
ggcacgaggg cagatcgatc gactcgagga ccacatcgca tc atg aag aac ttc       54
                                              Met Lys Asn Phe
                                                1 ctt ctg gcg tcc gcg ctg atc gcg gtt gcc gca gct cag cag agt gct     102
Leu Leu Ala Ser Ala Leu Ile Ala Val Ala Ala Ala Gln Gln Ser Ala
5               10                  15                  20 tgg gga cag tgc ggt gga att ggc tgg act ggc gcg acg act tgt atc     150
Trp Gly Gln Cys Gly Gly Ile Gly Trp Thr Gly Ala Thr Thr Cys Ile
            25                  30                  35 tct ggc tac acg tgc tca aag atc aac gac tac tat tcc cag tgc att     198
Ser Gly Tyr Thr Cys Ser Lys Ile Asn Asp Tyr Tyr Ser Gln Cys Ile
        40                  45                  50 ccg ggt acg gct tca acc acc act caa ggc ggc ggc aat ggc gga gga     246
Pro Gly Thr Ala Ser Thr Thr Thr Gln Gly Gly Gly Asn Gly Gly Gly
    55                  60                  65 aac ggc ggt aca acg act act ccc act acc act cca gcg gcc agt aac     294
Asn Gly Gly Thr Thr Thr Thr Pro Thr Thr Thr Pro Ala Ala Ser Asn
70                  75                  80 acc aac aac ccg ttc tcc ggc aag acc caa tgg gcg aac cct tac tac     342
Thr Asn Asn Pro Phe Ser Gly Lys Thr Gln Trp Ala Asn Pro Tyr Tyr
85                  90                  95                 100 gct tcc gag gtc tcg agc atc gcc atc ccg tcc ctc gtt gcc gcc gga     390
Ala Ser Glu Val Ser Ser Ile Ala Ile Pro Ser Leu Val Ala Ala Gly
                105                 110                 115 aac acc cac tac atc gtc gac caa ggc cgc agc ggc aag cag ccg acc     438
Asn Thr His Tyr Ile Val Asp Gln Gly Arg Ser Gly Lys Gln Pro Thr
            120                 125                 130 ggc cag ctc cag cag ggc gat tgg tgc aac gcc ctg gga acc ggc ttt     486
Gly Gln Leu Gln Gln Gly Asp Trp Cys Asn Ala Leu Gly Thr Gly Phe
        135                 140                 145
```

```
gga att cgt cct gat aca acc ccg gat gat ccc aac ctt gat gct ttc        534
Gly Ile Arg Pro Asp Thr Thr Pro Asp Asp Pro Asn Leu Asp Ala Phe
    150                 155                 160 gtg tgg gtt aag ccg ggt ggt gaa tcg gat ggt acc agc aat act tcc        582
Val Trp Val Lys Pro Gly Gly Glu Ser Asp Gly Thr Ser Asn Thr Ser
165                 170                 175                 180 tcg acc cgc tat gat tat cat tgt gga cag agc gat gcg cta caa ccg        630
Ser Thr Arg Tyr Asp Tyr His Cys Gly Gln Ser Asp Ala Leu Gln Pro
                185                 190                 195 gcc ccg gag gcg gga acg tgg ttc cag gcg tat ttt gtg cag ttg ctg        678
Ala Pro Glu Ala Gly Thr Trp Phe Gln Ala Tyr Phe Val Gln Leu Leu
        200                 205                 210 cag aat gct aat cct agc ttc acg taagcttggg agcgtggggg ttggaagatg       732
Gln Asn Ala Asn Pro Ser Phe Thr
            215                 220 tgtattgtat gtgtagatag agaaaaactg ttggcctatt caggactaag                 782

<210> SEQ ID NO 22
<211> LENGTH: 220
<212> TYPE: PRT
<213> ORGANISM: Trichophaea saccata

<400> SEQUENCE: 22

Met Lys Asn Phe Leu Leu Ala Ser Ala Leu Ile Ala Val Ala Ala Ala
1               5                   10                  15

Gln Gln Ser Ala Trp Gly Gln Cys Gly Gly Ile Gly Trp Thr Gly Ala
            20                  25                  30

Thr Thr Cys Ile Ser Gly Tyr Thr Cys Ser Lys Ile Asn Asp Tyr Tyr
        35                  40                  45

Ser Gln Cys Ile Pro Gly Thr Ala Ser Thr Thr Gln Gly Gly Gly
    50                  55                  60

Asn Gly Gly Gly Asn Gly Gly Thr Thr Thr Pro Thr Thr Thr Pro
65                  70                  75                  80

Ala Ala Ser Asn Thr Asn Asn Pro Phe Ser Gly Lys Thr Gln Trp Ala
            85                  90                  95

Asn Pro Tyr Tyr Ala Ser Glu Val Ser Ser Ile Ala Ile Pro Ser Leu
        100                 105                 110

Val Ala Ala Gly Asn Thr His Tyr Ile Val Asp Gln Gly Arg Ser Gly
        115                 120                 125

Lys Gln Pro Thr Gly Gln Leu Gln Gln Gly Asp Trp Cys Asn Ala Leu
    130                 135                 140

Gly Thr Gly Phe Gly Ile Arg Pro Asp Thr Thr Pro Asp Asp Pro Asn
145                 150                 155                 160

Leu Asp Ala Phe Val Trp Val Lys Pro Gly Gly Glu Ser Asp Gly Thr
                165                 170                 175

Ser Asn Thr Ser Ser Thr Arg Tyr Asp Tyr His Cys Gly Gln Ser Asp
            180                 185                 190

Ala Leu Gln Pro Ala Pro Glu Ala Gly Thr Trp Phe Gln Ala Tyr Phe
        195                 200                 205

Val Gln Leu Leu Gln Asn Ala Asn Pro Ser Phe Thr
    210                 215                 220

<210> SEQ ID NO 23
<211> LENGTH: 1587
<212> TYPE: DNA
<213> ORGANISM: Stibella annulata
<220> FEATURE:
```

-continued

```
<221> NAME/KEY: CDS
<222> LOCATION: (21)..(1394)

<400> SEQUENCE: 23
ggcacgaggc gcgcatcaca atg gcc ggt cga ttc ttc ctc tct gct gcc ttc        53
                     Met Ala Gly Arg Phe Phe Leu Ser Ala Ala Phe
                      1               5                  10 ctg gct agc gcg gct ttg gcc gtc cct ctc gag gag agg cag aac tgc         101
Leu Ala Ser Ala Ala Leu Ala Val Pro Leu Glu Glu Arg Gln Asn Cys
             15                  20                  25 tcc ccg cag tgg gcc cag tgc ggt gga aat gga tgg agc ggt ccg acg         149
Ser Pro Gln Trp Ala Gln Cys Gly Gly Asn Gly Trp Ser Gly Pro Thr
         30                  35                  40 tgc tgc gcc tcc ggc agc aac tgc cag gtc acc aac gag tgg tac tct         197
Cys Cys Ala Ser Gly Ser Asn Cys Gln Val Thr Asn Glu Trp Tyr Ser
 45                  50                  55 cag tgt gtt ccg ggc gcg gcg cct ccc cct ccc ccc gtc acc acg acg         245
Gln Cys Val Pro Gly Ala Ala Pro Pro Pro Pro Pro Val Thr Thr Thr
 60                  65                  70                  75 cgg tcg acc acc acg ccc ccg acg acg acc agg acc acc gct gat             293
Arg Ser Thr Thr Thr Pro Pro Thr Thr Thr Arg Thr Thr Ala Asp
                 80                  85                  90 gcc cct cct ccc acc ggc ggc gct act tac acc ggc aac ccc ttc ctc         341
Ala Pro Pro Pro Thr Gly Gly Ala Thr Tyr Thr Gly Asn Pro Phe Leu
                 95                 100                 105 ggt gtc aac cag tgg gcc aac aac ttc tac cgg tct gag atc atg aac         389
Gly Val Asn Gln Trp Ala Asn Asn Phe Tyr Arg Ser Glu Ile Met Asn
            110                 115                 120 atc gcc gtc ccg tcc ctg tcc ggt gcc atg gct acc gcc gcc gcc aag         437
Ile Ala Val Pro Ser Leu Ser Gly Ala Met Ala Thr Ala Ala Ala Lys
        125                 130                 135 gtc gcc gat gtg ccc acc ttc cag tgg att gac aag atg gac aag ctc         485
Val Ala Asp Val Pro Thr Phe Gln Trp Ile Asp Lys Met Asp Lys Leu
140                 145                 150                 155 ccc ttg atc gat gag gct ctc gcc gac gtc cgc gct gcc aac gcc cgt         533
Pro Leu Ile Asp Glu Ala Leu Ala Asp Val Arg Ala Ala Asn Ala Arg
                160                 165                 170 ggc ggc aac tac gct tcc atc ctg gtc gtc tac aac ctg ccc gac cgt         581
Gly Gly Asn Tyr Ala Ser Ile Leu Val Val Tyr Asn Leu Pro Asp Arg
            175                 180                 185 gac tgc gcc gcc gcc gcc tcg aac ggc gag ttc gcc atc gcc gac ggc         629
Asp Cys Ala Ala Ala Ala Ser Asn Gly Glu Phe Ala Ile Ala Asp Gly
        190                 195                 200 ggt gtt gct aag tac aag aac tac att gac gag att cgc aag ctc gtc         677
Gly Val Ala Lys Tyr Lys Asn Tyr Ile Asp Glu Ile Arg Lys Leu Val
    205                 210                 215 atc aag tac aac gac ctc cgt atc atc ctg gtc atc gag ccc gac tcc         725
Ile Lys Tyr Asn Asp Leu Arg Ile Ile Leu Val Ile Glu Pro Asp Ser
220                 225                 230                 235 ctc gcc aac atg gtg acc aac atg aac gtc gcc aag tgc cag aac gcc         773
Leu Ala Asn Met Val Thr Asn Met Asn Val Ala Lys Cys Gln Asn Ala
                240                 245                 250 gcc tcg gcc tac cgg gag tgc acc aac tat gcc ctg acg aac ctc gac         821
Ala Ser Ala Tyr Arg Glu Cys Thr Asn Tyr Ala Leu Thr Asn Leu Asp
            255                 260                 265 ctg ccc aac gtc gcc cag tac atg gat gcc gga cat gct ggc tgg ctc         869
Leu Pro Asn Val Ala Gln Tyr Met Asp Ala Gly His Ala Gly Trp Leu
        270                 275                 280 ggc tgg ccc gcc aac atc acc ccc gcc gcc cag ctc ttc gcc gag gtc         917
Gly Trp Pro Ala Asn Ile Thr Pro Ala Ala Gln Leu Phe Ala Glu Val
```

```
        285                 290                 295
tac aag cag gcc ggc agc ccc aag tcg gtc cgt ggt ctg gcc atc aac      965
Tyr Lys Gln Ala Gly Ser Pro Lys Ser Val Arg Gly Leu Ala Ile Asn
300                 305                 310                 315 gtc tcc aac tac aac gcg tgg agc gtt tcg tcc cct cct ccc tac acc     1013
Val Ser Asn Tyr Asn Ala Trp Ser Val Ser Ser Pro Pro Pro Tyr Thr
                320                 325                 330 tct ccc aac ccc aac tac gac gag cgc cac ttc gtt gag gcc ttt gcg     1061
Ser Pro Asn Pro Asn Tyr Asp Glu Arg His Phe Val Glu Ala Phe Ala
            335                 340                 345 ccc ctc ctg cgc cag aac ggc tgg gat gcc aag ttc atc gtc gac cag     1109
Pro Leu Leu Arg Gln Asn Gly Trp Asp Ala Lys Phe Ile Val Asp Gln
        350                 355                 360 ggc cgc tcc ggc agg cag ccc acc ggc cag cag gag tgg gga cac tgg     1157
Gly Arg Ser Gly Arg Gln Pro Thr Gly Gln Gln Glu Trp Gly His Trp
    365                 370                 375 tgc aac gcc atc ggc act ggc ttc ggc cag cgc ccg acg tcc aac acc     1205
Cys Asn Ala Ile Gly Thr Gly Phe Gly Gln Arg Pro Thr Ser Asn Thr
380                 385                 390                 395 ggc cac gcc gat gtt gac gct ttc gtc tgg atc aag ccg ggc ggt gag     1253
Gly His Ala Asp Val Asp Ala Phe Val Trp Ile Lys Pro Gly Gly Glu
                400                 405                 410 tgc gac ggc acc agc gac acc tcg gcc gcc cgc tac gac cac ttc tgt     1301
Cys Asp Gly Thr Ser Asp Thr Ser Ala Ala Arg Tyr Asp His Phe Cys
            415                 420                 425 ggc aac cct gat gcc ctc aag ccg gcc ccc gaa gcc gga gag tgg ttc     1349
Gly Asn Pro Asp Ala Leu Lys Pro Ala Pro Glu Ala Gly Glu Trp Phe
        430                 435                 440 cag gcc tac ttc gag cag ctt ctg cgc aac gcc aac ccc gcc ttc         1394
Gln Ala Tyr Phe Glu Gln Leu Leu Arg Asn Ala Asn Pro Ala Phe
    445                 450                 455 taagtgctgg atgagctttt ctgagagggt acttccgcgg tcttgggttt cactcttctc    1454
agcctttcag ggcagcagtt ttggtttctt ggggtaggac ctccgggttt atgtagacgg    1514
agttaggaag ccaaacctac tatgaatgta gtattcaaga agataatgac ttgaaaaaaa    1574
aaaaaaaaaa aaa                                                      1587

<210> SEQ ID NO 24
<211> LENGTH: 458
<212> TYPE: PRT
<213> ORGANISM: Stibella annulata

<400> SEQUENCE: 24

Met Ala Gly Arg Phe Phe Leu Ser Ala Ala Phe Leu Ala Ser Ala Ala
1               5                   10                  15

Leu Ala Val Pro Leu Glu Glu Arg Gln Asn Cys Ser Pro Gln Trp Ala
                20                  25                  30

Gln Cys Gly Gly Asn Gly Trp Ser Gly Pro Thr Cys Cys Ala Ser Gly
            35                  40                  45

Ser Asn Cys Gln Val Thr Asn Glu Trp Tyr Ser Gln Cys Val Pro Gly
        50                  55                  60

Ala Ala Pro Pro Pro Pro Val Thr Thr Thr Arg Ser Thr Thr Thr
65                  70                  75                  80

Pro Pro Thr Thr Thr Thr Arg Thr Thr Ala Asp Ala Pro Pro Thr
                85                  90                  95

Gly Gly Ala Thr Tyr Thr Gly Asn Pro Phe Leu Gly Val Asn Gln Trp
            100                 105                 110
```

Ala Asn Asn Phe Tyr Arg Ser Glu Ile Met Asn Ile Ala Val Pro Ser
            115                 120                 125

Leu Ser Gly Ala Met Ala Thr Ala Ala Ala Lys Val Ala Asp Val Pro
    130                 135                 140

Thr Phe Gln Trp Ile Asp Lys Met Asp Lys Leu Pro Leu Ile Asp Glu
145                 150                 155                 160

Ala Leu Ala Asp Val Arg Ala Ala Asn Ala Arg Gly Gly Asn Tyr Ala
                165                 170                 175

Ser Ile Leu Val Val Tyr Asn Leu Pro Asp Arg Asp Cys Ala Ala Ala
            180                 185                 190

Ala Ser Asn Gly Glu Phe Ala Ile Ala Asp Gly Gly Val Ala Lys Tyr
        195                 200                 205

Lys Asn Tyr Ile Asp Glu Ile Arg Lys Leu Val Ile Lys Tyr Asn Asp
    210                 215                 220

Leu Arg Ile Ile Leu Val Ile Glu Pro Asp Ser Leu Ala Asn Met Val
225                 230                 235                 240

Thr Asn Met Asn Val Ala Lys Cys Gln Asn Ala Ala Ser Ala Tyr Arg
                245                 250                 255

Glu Cys Thr Asn Tyr Ala Leu Thr Asn Leu Asp Leu Pro Asn Val Ala
            260                 265                 270

Gln Tyr Met Asp Ala Gly His Ala Gly Trp Leu Gly Trp Pro Ala Asn
        275                 280                 285

Ile Thr Pro Ala Ala Gln Leu Phe Ala Glu Val Tyr Lys Gln Ala Gly
    290                 295                 300

Ser Pro Lys Ser Val Arg Gly Leu Ala Ile Asn Val Ser Asn Tyr Asn
305                 310                 315                 320

Ala Trp Ser Val Ser Ser Pro Pro Tyr Thr Ser Pro Asn Pro Asn
                325                 330                 335

Tyr Asp Glu Arg His Phe Val Glu Ala Phe Ala Pro Leu Leu Arg Gln
            340                 345                 350

Asn Gly Trp Asp Ala Lys Phe Ile Val Asp Gln Gly Arg Ser Gly Arg
        355                 360                 365

Gln Pro Thr Gly Gln Gln Glu Trp Gly His Trp Cys Asn Ala Ile Gly
    370                 375                 380

Thr Gly Phe Gly Gln Arg Pro Thr Ser Asn Thr Gly His Ala Asp Val
385                 390                 395                 400

Asp Ala Phe Val Trp Ile Lys Pro Gly Gly Glu Cys Asp Gly Thr Ser
                405                 410                 415

Asp Thr Ser Ala Ala Arg Tyr Asp His Phe Cys Gly Asn Pro Asp Ala
            420                 425                 430

Leu Lys Pro Ala Pro Glu Ala Gly Glu Trp Phe Gln Ala Tyr Phe Glu
        435                 440                 445

Gln Leu Leu Arg Asn Ala Asn Pro Ala Phe
    450                 455

<210> SEQ ID NO 25
<211> LENGTH: 1559
<212> TYPE: DNA
<213> ORGANISM: Malbrancheae cinnamonea
<220> FEATURE:
<221> NAME/KEY: CDS
<222> LOCATION: (41)..(1210)

<400> SEQUENCE: 25
cgaggcgtcc atcccacgcc gcacgcgtca gccagtcatt atg aga gac tct ttg      55
                                            Met Arg Asp Ser Leu -continued

```
                        1               5
ttc act ttg cta tct ctt gcc ttg ggc tcg gcc tct gcc agc cct ttc      103
Phe Thr Leu Leu Ser Leu Ala Leu Gly Ser Ala Ser Ala Ser Pro Phe
                10                  15                  20 ctt ctt cca agg caa gcg aac tcc tcc aac ccg ttt gct gga cac acg      151
Leu Leu Pro Arg Gln Ala Asn Ser Ser Asn Pro Phe Ala Gly His Thr
            25                  30                  35 atc tat cca aac ccg tac tac tcc aac gag att gac gag ttt gcc att      199
Ile Tyr Pro Asn Pro Tyr Tyr Ser Asn Glu Ile Asp Glu Phe Ala Ile
        40                  45                  50 ccc gcg ctg caa gag acc gat cct gca ctt gtg gag aag gcc gct tta      247
Pro Ala Leu Gln Glu Thr Asp Pro Ala Leu Val Glu Lys Ala Ala Leu
    55                  60                  65 gta aaa gaa gtt gga act ttc ttc tgg att gat gtc gtc gcc aag gtc      295
Val Lys Glu Val Gly Thr Phe Phe Trp Ile Asp Val Val Ala Lys Val
70                  75                  80                  85 cca gat atc ggc cct tac ctg cag ggg atc caa gaa gca aac gcc gca      343
Pro Asp Ile Gly Pro Tyr Leu Gln Gly Ile Gln Glu Ala Asn Ala Ala
                90                  95                  100 ggc cag aat ccg ccg tac atc ggc gcg att gtt gtc tat gac ctc ccc      391
Gly Gln Asn Pro Pro Tyr Ile Gly Ala Ile Val Val Tyr Asp Leu Pro
            105                 110                 115 aac cgt gac tgc gct gcc gca gct tcc aac gga gag ttc agc ctc gag      439
Asn Arg Asp Cys Ala Ala Ala Ala Ser Asn Gly Glu Phe Ser Leu Glu
        120                 125                 130 gat ggc ggc gag gag aag tac cgc ggt tat atc gac ggt atc cgg gag      487
Asp Gly Gly Glu Glu Lys Tyr Arg Gly Tyr Ile Asp Gly Ile Arg Glu
    135                 140                 145 caa att gag aaa tac cca gac gtc cgt gtc gcg ctg gtt atc gag ccc      535
Gln Ile Glu Lys Tyr Pro Asp Val Arg Val Ala Leu Val Ile Glu Pro
150                 155                 160                 165 gat tcg ctc gcg aac atg gtc acc aat ctc aat gtc ccc aag tgc gct      583
Asp Ser Leu Ala Asn Met Val Thr Asn Leu Asn Val Pro Lys Cys Ala
                170                 175                 180 gag tcg gag cag gct tat cga gat ggc gtc gcg tat gca ctg aaa cag      631
Glu Ser Glu Gln Ala Tyr Arg Asp Gly Val Ala Tyr Ala Leu Lys Gln
            185                 190                 195 cta gac ctc ccc aac gtc tgg aca tat atc gat gct ggt cat tca ggt      679
Leu Asp Leu Pro Asn Val Trp Thr Tyr Ile Asp Ala Gly His Ser Gly
        200                 205                 210 tgg ctt ggc tgg ccc gcc aac atc gag cct gcc gca gaa att ttt gtt      727
Trp Leu Gly Trp Pro Ala Asn Ile Glu Pro Ala Ala Glu Ile Phe Val
    215                 220                 225 gag gtc tgg aat gca gct ggc agg cca aag tcc act cga ggg ttt gct      775
Glu Val Trp Asn Ala Ala Gly Arg Pro Lys Ser Thr Arg Gly Phe Ala
230                 235                 240                 245 acg aac gtt tcc aac tac aac ggt tat tcc ctc agc acc gct cct ccc      823
Thr Asn Val Ser Asn Tyr Asn Gly Tyr Ser Leu Ser Thr Ala Pro Pro
                250                 255                 260 tac act gag ccc aac ccc aat ttc gac gaa gtg cgt tat atc aat gca      871
Tyr Thr Glu Pro Asn Pro Asn Phe Asp Glu Val Arg Tyr Ile Asn Ala
            265                 270                 275 ttc cgc cca ctc ctc gag gca cgg ggt ttc cca gca tac ttc atc gtc      919
Phe Arg Pro Leu Leu Glu Ala Arg Gly Phe Pro Ala Tyr Phe Ile Val
        280                 285                 290 gac caa ggc cgc agc ggt gtc cag ccc act gcg cag att gag caa gga      967
Asp Gln Gly Arg Ser Gly Val Gln Pro Thr Ala Gln Ile Glu Gln Gly
    295                 300                 305 cac tgg tgc aat gtg atc gac acc ggt ttt gga act cgc ccc act act     1015
```

```
His Trp Cys Asn Val Ile Asp Thr Gly Phe Gly Thr Arg Pro Thr Thr
310                 315                 320                 325 gac act ggt aat gag tac gtt gac tcg atc gtg tgg gtg aag cct ggc    1063
Asp Thr Gly Asn Glu Tyr Val Asp Ser Ile Val Trp Val Lys Pro Gly
            330                 335                 340 ggc gaa tcg gac gga acc agc gat acc tct gct gag aga tat gac tac    1111
Gly Glu Ser Asp Gly Thr Ser Asp Thr Ser Ala Glu Arg Tyr Asp Tyr
345                 350                 355 cac tgc gga ctt gag gat gca ttg aag cca gct cct gaa gcg gga cag    1159
His Cys Gly Leu Glu Asp Ala Leu Lys Pro Ala Pro Glu Ala Gly Gln
    360                 365                 370 tgg ttc cag gcc tac ttc gag caa ctg ctc aga aat gcc aac ccc cca    1207
Trp Phe Gln Ala Tyr Phe Glu Gln Leu Leu Arg Asn Ala Asn Pro Pro
375                 380                 385 ttc taaatcagat gaaggacgga cccaattgat gacggcctgt cttcgtgatc         1260
Phe
390 cgacgaaagc aatgtcaggg tgaaaatgac cgagagattg gagagtcatg aggataggta  1320 gtcaatgatt tcacccgagt ttccacgttt tacccttctt gtacatagtt tggagtcgcc  1380 tgttggtttc agtagtacat cttatccgac agagtctatc gtttgattac cccagtcaaa  1440 agcgttattg caatctttc ctagggattt attgtttgct gcggatgtcg tggctatggg   1500 cagctgactg aattaaactg gaactcttgg tatccaaaaa aaaaaaaaaa aaaaaaaa    1559

<210> SEQ ID NO 26
<211> LENGTH: 390
<212> TYPE: PRT
<213> ORGANISM: Malbrancheae cinnamonea

<400> SEQUENCE: 26

Met Arg Asp Ser Leu Phe Thr Leu Leu Ser Leu Ala Leu Gly Ser Ala
1               5                   10                  15

Ser Ala Ser Pro Phe Leu Leu Pro Arg Gln Ala Asn Ser Ser Asn Pro
            20                  25                  30

Phe Ala Gly His Thr Ile Tyr Pro Asn Pro Tyr Tyr Ser Asn Glu Ile
        35                  40                  45

Asp Glu Phe Ala Ile Pro Ala Leu Gln Glu Thr Asp Pro Ala Leu Val
    50                  55                  60

Glu Lys Ala Ala Leu Val Lys Glu Val Gly Thr Phe Phe Trp Ile Asp
65                  70                  75                  80

Val Val Ala Lys Val Pro Asp Ile Gly Pro Tyr Leu Gln Gly Ile Gln
                85                  90                  95

Glu Ala Asn Ala Ala Gly Gln Asn Pro Pro Tyr Ile Gly Ala Ile Val
            100                 105                 110

Val Tyr Asp Leu Pro Asn Arg Asp Cys Ala Ala Ala Ser Asn Gly
        115                 120                 125

Glu Phe Ser Leu Glu Asp Gly Gly Glu Glu Lys Tyr Arg Gly Tyr Ile
    130                 135                 140

Asp Gly Ile Arg Glu Gln Ile Glu Lys Tyr Pro Asp Val Arg Val Ala
145                 150                 155                 160

Leu Val Ile Glu Pro Asp Ser Leu Ala Asn Met Val Thr Asn Leu Asn
                165                 170                 175

Val Pro Lys Cys Ala Glu Ser Glu Gln Ala Tyr Arg Asp Gly Val Ala
            180                 185                 190

Tyr Ala Leu Lys Gln Leu Asp Leu Pro Asn Val Trp Thr Tyr Ile Asp
        195                 200                 205
```

Ala Gly His Ser Gly Trp Leu Gly Trp Pro Ala Asn Ile Glu Pro Ala
    210                 215                 220

Ala Glu Ile Phe Val Glu Val Trp Asn Ala Ala Gly Arg Pro Lys Ser
225                 230                 235                 240

Thr Arg Gly Phe Ala Thr Asn Val Ser Asn Tyr Asn Gly Tyr Ser Leu
                245                 250                 255

Ser Thr Ala Pro Pro Tyr Thr Glu Pro Asn Pro Asn Phe Asp Glu Val
            260                 265                 270

Arg Tyr Ile Asn Ala Phe Arg Pro Leu Leu Glu Ala Arg Gly Phe Pro
        275                 280                 285

Ala Tyr Phe Ile Val Asp Gln Gly Arg Ser Gly Val Gln Pro Thr Ala
    290                 295                 300

Gln Ile Glu Gln Gly His Trp Cys Asn Val Ile Asp Thr Gly Phe Gly
305                 310                 315                 320

Thr Arg Pro Thr Thr Asp Thr Gly Asn Glu Tyr Val Asp Ser Ile Val
                325                 330                 335

Trp Val Lys Pro Gly Gly Glu Ser Asp Gly Thr Ser Asp Thr Ser Ala
            340                 345                 350

Glu Arg Tyr Asp Tyr His Cys Gly Leu Glu Asp Ala Leu Lys Pro Ala
        355                 360                 365

Pro Glu Ala Gly Gln Trp Phe Gln Ala Tyr Phe Glu Gln Leu Leu Arg
    370                 375                 380

Asn Ala Asn Pro Pro Phe
385                 390

<210> SEQ ID NO 27
<211> LENGTH: 17
<212> TYPE: DNA
<213> ORGANISM: Chaetomium thermophilum
<220> FEATURE:
<221> NAME/KEY: misc_feature
<222> LOCATION: (1)..(17)
<223> OTHER INFORMATION: r is a or g
      y is t or c
      n is a, g, t, or c

<400> SEQUENCE: 27
tggggncart gyggngg                                                  17

<210> SEQ ID NO 28
<211> LENGTH: 17
<212> TYPE: DNA
<213> ORGANISM: Chaetomium thermophilum
<220> FEATURE:
<221> NAME/KEY: misc_feature
<222> LOCATION: (1)..(17)
<223> OTHER INFORMATION: y is t or c
      n is a, g, t, or c

<400> SEQUENCE: 28
tggytnggnt ggccngc                                                  17

<210> SEQ ID NO 29
<211> LENGTH: 17
<212> TYPE: DNA
<213> ORGANISM: Chaetomium thermophilum
<220> FEATURE:
<221> NAME/KEY: misc_feature
<222> LOCATION: (1)..(17)
<223> OTHER INFORMATION: n is a, g, t, or c
      r is a or g

```
<400> SEQUENCE: 29
gcnggccanc cnarcca                                                  17

<210> SEQ ID NO 30
<211> LENGTH: 17
<212> TYPE: DNA
<213> ORGANISM: Chaetomium thermophilum
<220> FEATURE:
<221> NAME/KEY: misc_feature
<222> LOCATION: (1)..(17)
<223> OTHER INFORMATION: r is a or g
      n is a, g, t, or c

<400> SEQUENCE: 30
ttrcaccart cncccca                                                  17

<210> SEQ ID NO 31
<211> LENGTH: 17
<212> TYPE: DNA
<213> ORGANISM: Chaetomium thermophilum
<220> FEATURE:
<221> NAME/KEY: misc_feature
<222> LOCATION: (1)..(17)
<223> OTHER INFORMATION: r is a or g
      y is t or c
      n is a, g, t or c

<400> SEQUENCE: 31
ggyttnaccc anacraa                                                  17

<210> SEQ ID NO 32
<211> LENGTH: 17
<212> TYPE: DNA
<213> ORGANISM: Chaetomium thermophilum
<220> FEATURE:
<221> NAME/KEY: misc_feature
<222> LOCATION: (1)..(17)
<223> OTHER INFORMATION: r is a or g
      y is t or c
      n is a, g, t or c

<400> SEQUENCE: 32
aartangcyt graacca                                                  17

<210> SEQ ID NO 33
<211> LENGTH: 25
<212> TYPE: DNA
<213> ORGANISM: Malbranchia cinnamonea

<400> SEQUENCE: 33
gggtcatgag agactctttg ttcac                                         25

<210> SEQ ID NO 34
<211> LENGTH: 34
<212> TYPE: DNA
<213> ORGANISM: Malbranchia cinnamonea

<400> SEQUENCE: 34
gggttaatta attagaatgg ggggttggca tttc                               34

<210> SEQ ID NO 35
<211> LENGTH: 31
<212> TYPE: DNA
<213> ORGANISM: Stilbella anulata

<400> SEQUENCE: 35
```

```
actggattta ccatggccgg tcgattcttc c                              31
```

<210> SEQ ID NO 36
<211> LENGTH: 31
<212> TYPE: DNA
<213> ORGANISM: Stilbella anulata

<400> SEQUENCE: 36

```
agtcacctct agttattaga aggcggggtt g                              31
```